United States Patent [19]
Davidson

[11] Patent Number: 5,981,484
[45] Date of Patent: Nov. 9, 1999

[54] ANTIANGIOGENIC PEPTIDES AND METHODS FOR INHIBITING ANGIOGENESIS

[75] Inventor: Donald J. Davidson, Gurnee, Ill.

[73] Assignee: Abbott Laboratories, Abbott Park, Ill.

[21] Appl. No.: 08/832,087

[22] Filed: Apr. 3, 1997

Related U.S. Application Data

[63] Continuation-in-part of application No. 08/643,219, May 3, 1996, Pat. No. 5,801,146.
[51] Int. Cl.$^6$ .......................... A61K 38/00; A61K 38/04
[52] U.S. Cl. ........................... 514/12; 530/300; 530/324; 530/325; 530/326; 530/327; 530/328; 530/329; 530/330
[58] Field of Search ................................ 530/300, 324, 530/325, 326, 327, 328, 329, 330; 514/12

[56] References Cited

U.S. PATENT DOCUMENTS

| | | | |
|---|---|---|---|
| 5,512,591 | 4/1996 | Halperin et al. | 514/399 |
| 5,854,221 | 12/1998 | Cao et al. | 514/12 |

FOREIGN PATENT DOCUMENTS

| | | |
|---|---|---|
| 9204450 | 3/1992 | WIPO . |
| 9529242 | 11/1995 | WIPO . |
| 9723500 | 2/1997 | WIPO . |

OTHER PUBLICATIONS

Scrip 2120:21 (Apr. 16, 1996).
Fidler, I.J., et al., "The Implications of Angiogenesis for the Biology and Therapy of Cancer Metastasis", *Cell*, 79:185–188 (1994).
Folkman, J., "Clinical Applications of Research on Angiogenesis", *The New England Journal of Medicine*, 333(26):1757–1763 (1995).
Folkman, J., et al., "Angiogenesis", *Journ. of Biological Chemistry*, 267(16):10931–10934 (1992).
Folkman, J., et al., "Angiogenic Factors", *Science*, 235:442–447 (1987).
Gasparini, G., et al., "Clinical Importance of the Determination of Tumor Angiogenesis in Breast Carcinoma: Much More Than a New Prognostic Tool", *Journ. of Clinical Oncology*, 13(3):765–782 (1995).
Sottrup–Jensen, L., et al., "The Primary Structure of Human Plasminogen: Isolation of Two Lysine–Binding Fragments and One "Mini–" Plasminogen (MW, 38,000) by Elastase––Catalyzed–Specific Limited Proteolysis", *Progress in Chemical Fibrinolysis and Thrombolysis*, 3:191–209 (1978).
Kolberg, R., "Angogenic Inhibitor Loss May Be Key To Post–Surgery Metastasis", *Journal of NIH Research*, 8:31–33 (1994).
Menhart, N., et al., "Functional Independence of the Kringle 4 and Kringle 5 Regions of Human Plasminogen", *Biochemistry*, 32:8799–8806 (1993).

Novokhatny, V. V., et al., "Domains in Human Plasminogen", *J. Mol. Biol.*, 179:215–232 (1984).
O'Reilly, M. S., et al., "Angiostatin: A Novel Angiogenesis Inhibitor That Mediates the Suppression of Metastases by a Lewis Lung Carcinoma", *Cell*, 79:315–328 (1994).
Teicher, B. A., et al., "Antiangiogenic Agents Can Increase Tumor Oxygenation and Response to Radiation Therapy", *Radiation Oncology Investigations*, 2:269–276 (1995).
Teicher, B. A., et al., "Antiangiogenic Agents Potentiate Cytotoxic Cancer Therapies against Primary and Metastatic Disease", *Cancer Research*, 52:6702–6704 (1992).
Teicher, B. A., et al., "Antiangiogenic Treatment (TNP–470/Minocycline) Increases Tissue Levels of Anticancer Drugs in Mice Bearing Lewis Lung Carcinoma", *Oncology Research*, 7(5):237–243 (1995).
Teicher, B. A., et al., "β–Cyclodextrin tetradecasulfate/tetrahydrocortisol ± minocycline as modulators of cancer therapies in vitro and in vivo against primary and metastatic lewis lung carcinoma", *Cancer Chemother Pharmacol*, 33:299–239 (1993).
Teicher, B. A., et al., "Influence of an Anti–Angiogenic Treatment on 9L Gliosarcoma: Oxygenation and Response to Cytotoxic Therapy", *Int. J. Cancer*, 61:732–737 (1995).
Teicher, B. A., et al., "Potentiation of Cytotoxic Cancer Therapies by TNP–470 Alone and With Other Anti–Angiogenic Agents", *Int. J. Cancer*, 57:920–925 (1994).
Teicher, B. A., et al., "Potentiation of cytotoxic therapies by TNP–470 and minocycline in mice bearing EMT–6 mammary carcinoma", *Breast Cancer Research and Treatment*, 36:227–236 (1995).
Thewest, T., et al., "Ligand Interactions with the Kringle 5 Domain of Plasminogen", *Journal of Biological Chemistry*, 265(7):3906–3915 (1990).
Weidner, N., et al., "Tumor Angiogenesis and Metastasis—Correlation in Invasive Breast Carcinoma", *The New England Journal of Medicine*, 324(1):1–8 (1991).
McCance, S., et al., "Amino acid residues of the Kringle–4 and Kringle–5 domains of human plasminogen that stabilize their interactions with omega–amino acid ligands", *Journal of Biological Chemistry*, 269:32405–32410 (1994).
Thewes, T., et al., "Isolation, purification and 1H–NMR characterization of a kringle 5 domain fragment from human plasminogen", *Database Medline*, 1987.
Váradi, A., et al., "Kringle 5 of human plasminogen carries a benzamidine–binding site", *Biochemical and biophysical Research Communications*, 103:97–102 (1981).

*Primary Examiner*—Rebecca E. Prouty
*Assistant Examiner*—Einar Stole
*Attorney, Agent, or Firm*—Gregory W. Steele; Dianne Casuto

[57] ABSTRACT

Mammalian kringle 5 peptide fragments are disclosed for treating angiogenic diseases Methods and compositions for inhibiting angiogenic diseases are also disclosed.

12 Claims, 12 Drawing Sheets

| | | | | | | | | | | | | | | |
|---|---|---|---|---|---|---|---|---|---|---|---|---|---|---|
| GLU | PRO | LEU | ASP | ASP | TYR | VAL | ASN | THR | GLN | GLY | ALA | SER | LEU | PHE |
| 1 | | | | 5 | | | | | 10 | | | | | 15 |
| SER | VAL | THR | LYS | LYS | GLN | LEU | GLY | ALA | GLY | SER | ILE | GLU | GLU | CYS |
| | | | | 20 | | | | | 25 | | | | | 30 |
| ALA | ALA | LYS | CYS | GLU | GLU | ASP | GLU | GLU | PHE | THR | CYS | ARG | ALA | PHE |
| | | | | 35 | | | | | 40 | | | | | 45 |
| GLN | TYR | HIS | SER | LYS | GLU | GLN | GLN | CYS | VAL | ILE | MET | ALA | GLU | ASN |
| | | | | 50 | | | | | 55 | | | | | 60 |
| ARG | LYS | SER | SER | ILE | ILE | ILE | ARG | MET | ARG | ASP | VAL | VAL | LEU | PHE |
| | | | | 65 | | | | | 70 | | | | | 75 |
| GLU | LYS | LYS | VAL | TYR | LEU | SER | GLU | CYS | LYS | THR | GLY | ASN | GLY | LYS |
| | | | | 80 | | | | | 85 | | | | | 90 |
| ASN | TYR | ARG | GLY | THR | MET | SER | LYS | THR | LYS | ASN | GLY | ILE | THR | CYS |
| | | | | 95 | | | | | 100 | | | | | 105 |
| GLN | LYS | TRP | SER | SER | THR | SER | PRO | HIS | ARG | PRO | ARG | PHE | SER | PRO |
| | | | | 110 | | | | | 115 | | | | | 120 |
| ALA | THR | HIS | PRO | SER | GLU | GLY | LEU | GLU | GLU | ASN | TYR | CYS | ARG | ASN |
| | | | | 125 | | | | | 130 | | | | | 135 |
| PRO | ASP | ASN | ASP | PRO | GLN | GLY | PRO | TRP | CYS | TYR | THR | THR | ASP | PRO |
| | | | | 140 | | | | | 145 | | | | | 150 |
| GLU | LYS | ARG | TYR | ASP | TYR | CYS | ASP | ILE | LEU | GLU | CYS | GLU | GLU | GLU |
| | | | | 155 | | | | | 160 | | | | | 165 |
| CYS | MET | HIS | CYS | SER | GLY | GLU | ASN | TYR | ASP | GLY | LYS | ILE | SER | LYS |
| | | | | 170 | | | | | 175 | | | | | 180 |
| THR | MET | SER | GLY | LEU | GLU | CYS | GLN | ALA | TRP | ASP | SER | GLN | SER | PRO |
| | | | | 185 | | | | | 190 | | | | | 195 |
| HIS | ALA | HIS | GLY | TYR | ILE | PRO | SER | LYS | PHE | PRO | ASN | LYS | ASN | LEU |
| | | | | 200 | | | | | 205 | | | | | 210 |
| LYS | LYS | ASN | TYR | CYS | ARG | ASN | PRO | ASP | ARG | GLU | LEU | ARG | PRO | TRP |
| | | | | 215 | | | | | 220 | | | | | 225 |
| CYS | PHE | THR | THR | ASP | PRO | ASN | LYS | ARG | TRP | GLU | LEU | CYS | ASP | ILE |
| | | | | 230 | | | | | 235 | | | | | 240 |
| PRO | ARG | CYS | THR | THR | PRO | PRO | PRO | SER | SER | GLY | PRO | THR | TYR | GLN |
| | | | | 245 | | | | | 250 | | | | | 255 |
| CYS | LEU | LYS | GLY | THR | GLY | GLU | ASN | TYR | ARG | GLY | ASN | VAL | ALA | VAL |
| | | | | 260 | | | | | 265 | | | | | 270 |

(SEQ ID NO:1)

FIG.1a

```
THR VAL SER GLY HIS THR CYS GLN HIS TRP SER ALA GLN THR PRO
                 275             280                 285

HIS THR HIS ASN ARG THR PRO GLU ASN PHE PRO CYS LYS ASN LEU
                 290             295                 300

ASP GLU ASN TYR CYS ARG ASN PRO ASP GLY LYS ARG ALA PRO TRP
                 305             310                 315

CYS HIS THR THR ASN SER GLN VAL ARG TRP GLU TYR CYS LYS ILE
                 320             325                 330

PRO SER CYS ASP SER SER PRO VAL SER THR GLU GLN LEU ALA PRO
                 335             340                 345

THR ALA PRO PRO GLU LEU THR PRO VAL VAL GLN ASP CYS TYR HIS
                 350             355                 360

GLY ASP GLY GLN SER TYR ARG GLY THR SER SER THR THR THR THR
                 365             370                 375

GLY LYS LYS CYS GLN SER TRP SER SER MET THR PRO HIS ARG HIS
                 380             385                 390

GLN LYS THR PRO GLU ASN TYR PRO ASN ALA GLY LEU THR MET ASN
                 395             400                 405

TYR CYS ARG ASN PRO ASP ALA ASP LYS GLY PRO TRP CYS PHE THR
                 410             415                 420

THR ASP PRO SER VAL ARG TRP GLU TYR CYS ASN LEU LYS LYS CYS
                 425             430                 435

SER GLY THR GLU ALA SER VAL VAL ALA PRO PRO VAL VAL LEU
                 440             445                 450

LEU PRO ASP VAL GLU THR PRO SER GLU GLU ASP CYS MET PHE GLY
                 455             460                 465

ASN GLY LYS GLY TYR ARG GLY LYS ARG ALA THR THR VAL THR GLY
                 470             475                 480

THR PRO CYS GLN ASP TRP ALA ALA GLN GLU PRO HIS ARG HIS SER
                 485             490                 495

ILE PHE THR PRO GLU THR ASN PRO ARG ALA GLY LEU GLU LYS ASN
                 500             505                 510

TYR CYS ARG ASN PRO ASP GLY ASP VAL GLY GLY PRO TRP CYS TYR
                 515             520                 525

THR THR ASN PRO ARG LYS LEU TYR ASP TYR CYS ASP VAL PRO GLN
                 530             535                 540
```

FIG.1b

CYS ALA ALA PRO SER PHE ASP CYS GLY LYS PRO GLN VAL GLU PRO
              545               550                   555

LYS LYS CYS PRO GLY ARG VAL VAL GLY GLY CYS VAL ALA HIS PRO
              560               565                   570

HIS SER TRP PRO TRP GLN VAL SER LEU ARG THR ARG PHE GLY MET
              575               580                   585

HIS PHE CYS GLY GLY THR LEU ILE SER PRO GLU TRP VAL LEU THR
              590               595                   600

ALA ALA HIS CYS LEU GLU LYS SER PRO ARG PRO SER SER TYR LYS
              605               610                   615

VAL ILE LEU GLY ALA HIS GLN GLU VAL ASN LEU GLU PRO HIS VAL
              620               625                   630

GLN GLU ILE GLU VAL SER ARG LEU PHE LEU GLU PRO THR ARG LYS
              635               640                   645

ASP ILE ALA LEU LEU LYS LEU SER SER PRO ALA VAL ILE THR ASP
              650               655                   660

LYS VAL ILE PRO ALA CYS LEU PRO SER PRO ASN TYR VAL VAL ALA
              665               670                   675

ASP ARG THR GLU CYS PHE ILE THR GLY TRP GLY GLU THR GLN GLY
              680               685                   690

THR PHE GLY ALA GLY LEU LEU LYS GLU ALA GLN LEU PRO VAL ILE
              695               700                   705

GLU ASN LYS VAL CYS ASN ARG TYR GLU PHE LEU ASN GLY ARG VAL
              710               715                   720

GLN SER THR GLU LEU CYS ALA GLY HIS LEU ALA GLY GLY THR ASP
              725               730                   735

SER CYS GLN GLY ASP SER GLY GLY PRO LEU VAL CYS PHE GLU LYS
              740               745                   750

ASP LYS TYR ILE LEU GLN GLY VAL THR SER TRP GLY LEU GLY CYS
              755               760                   765

ALA ARG PRO ASN LYS PRO GLY VAL TYR VAL ARG VAL SER ARG PHE
              770               775                   780

VAL THR TRP ILE GLU GLY VAL MET ARG ASN ASN
              785               790

Sequence alignment (positions 1–50+):

| Species | SEQ ID | | | | | 1 | | | | 5 | | | | | 10 |
|---|---|---|---|---|---|---|---|---|---|---|---|---|---|---|---|
| Human | (SEQ ID NO:2) | ASP | VAL | GLU | THR | VAL | ALA | PRO | PRO | PRO | VAL | VAL | LEU | LEU | PRO |
| Mouse | (SEQ ID NO:8) | SER | GLY | PRO | SER | --- | GLU | LEU | --- | THR | --- | SER | GLN | GLU | --- |
| Monkey | (SEQ ID NO:9) | --- | ALA | --- | --- | --- | --- | --- | ALA | --- | --- | ALA | GLN | --- | --- |
| Bovine | (SEQ ID NO:10) | GLY | --- | ASN | --- | PRO | --- | --- | --- | 000 | 000 | 000 | GLN | ALA | --- |
| Porcine | (SEQ ID NO:11) | SER | --- | ASP | LEU | THR | ASN | PHE | --- | ALA | ILE | ALA | GLN | VAL | --- |

| Species | | | | 15 | | | | | 20 | | | | |
|---|---|---|---|---|---|---|---|---|---|---|---|---|---|
| Human | PRO | SER | GLU | ASP | SER | GLU | GLU | ALA | CYS | MET | PHE | GLY | ASN |
| Mouse | --- | --- | --- | --- | --- | THR | --- | --- | --- | --- | --- | TYR | --- |
| Monkey | --- | --- | --- | --- | --- | --- | --- | --- | --- | --- | --- | --- | --- |
| Bovine | ASN | --- | --- | PRO | --- | ALA | --- | --- | --- | --- | --- | ILE | THR |
| Porcine | ASP | --- | --- | LEU | --- | 000 | --- | --- | --- | --- | --- | --- | --- |

| Species | 25 | | | | | 30 | | | | | 35 | | | |
|---|---|---|---|---|---|---|---|---|---|---|---|---|---|---|
| Human | GLY | LYS | GLY | TYR | ARG | GLY | LYS | ARG | ALA | THR | THR | VAL | THR | GLY |
| Mouse | --- | --- | ASP | --- | --- | --- | --- | THR | --- | --- | VAL | ALA | ALA | --- |
| Monkey | --- | --- | --- | --- | --- | --- | --- | LYS | --- | --- | --- | --- | --- | --- |
| Bovine | --- | --- | SER | --- | --- | --- | --- | LYS | --- | --- | --- | --- | ALA | --- |
| Porcine | --- | --- | ARG | --- | --- | --- | --- | --- | --- | --- | --- | --- | ALA | --- |

| Species | | 40 | | | | | 45 | | | | | 50 | | |
|---|---|---|---|---|---|---|---|---|---|---|---|---|---|---|
| Human | THR | PRO | CYS | GLN | ASP | TRP | ALA | ALA | GLN | GLU | PRO | HIS | ARG | HIS |
| Mouse | --- | --- | --- | --- | GLY | --- | --- | --- | --- | --- | --- | --- | --- | --- |
| Monkey | --- | --- | --- | --- | GLU | --- | --- | --- | --- | --- | --- | --- | SER | --- |
| Bovine | VAL | --- | --- | --- | GLU | --- | --- | --- | --- | --- | --- | --- | HIS | --- |
| Porcine | VAL | --- | --- | --- | GLU | --- | --- | --- | --- | --- | --- | --- | --- | --- |

|  | | | | | 55 | | | | | 60 | | | | | 65 | |
|---|---|---|---|---|---|---|---|---|---|---|---|---|---|---|---|---|
| Human | SER | ILE | PHE | THR | PRO | GLU | THR | ASN | PRO | ARG | ALA | GLY | LEU | GLU |
| Mouse | --- | --- | --- | --- | --- | GLN | --- | --- | --- | --- | --- | --- | --- | --- |
| Monkey | ARG | --- | --- | --- | --- | --- | --- | --- | --- | --- | --- | --- | --- | --- |
| Bovine | --- | --- | --- | --- | --- | --- | --- | --- | --- | GLN | SER | --- | --- | --- |
| Porcine | --- | --- | --- | --- | --- | --- | --- | --- | --- | --- | --- | --- | --- | --- |

|  | | | | 70 | | | | | 75 | | | | | 80 | |
|---|---|---|---|---|---|---|---|---|---|---|---|---|---|---|---|
| Human | LYS | ASN | TYR | CYS | ARG | ASN | PRO | ASP | GLY | ASP | VAL | GLY | GLY | PRO |
| Mouse | --- | --- | --- | --- | --- | --- | --- | --- | --- | --- | --- | ASN | --- | --- |
| Monkey | --- | --- | --- | --- | --- | --- | --- | --- | --- | --- | --- | --- | --- | --- |
| Bovine | ARG | --- | --- | --- | --- | --- | --- | --- | --- | --- | --- | ASN | --- | --- |
| Porcine | --- | --- | --- | --- | --- | --- | --- | --- | --- | --- | ASP | ASN | --- | --- |

|  | | | | 85 | | | | | 90 | | | | | | |
|---|---|---|---|---|---|---|---|---|---|---|---|---|---|---|---|
| Human | TRP | CYS | TYR | THR | THR | ASN | PRO | ARG | LYS | LEU | TYR | ASP | TYR | CYS |
| Mouse | --- | --- | --- | --- | --- | --- | --- | --- | --- | --- | --- | --- | --- | --- |
| Monkey | --- | --- | --- | --- | --- | --- | --- | --- | --- | --- | PHE | --- | --- | --- |
| Bovine | --- | --- | --- | --- | MET | --- | --- | --- | --- | --- | PHE | --- | --- | --- |
| Porcine | --- | --- | --- | --- | --- | --- | --- | --- | --- | GLN | PHE | --- | --- | --- |

|  | 95 | | | | | 100 | | 101 |
|---|---|---|---|---|---|---|---|---|
| Human | ASP | VAL | PRO | GLN | CYS | ALA | 000 | ALA |
| Mouse | --- | ILE | --- | LEU | --- | --- | SER | --- |
| Monkey | --- | --- | --- | --- | --- | --- | 000 | --- |
| Bovine | --- | --- | --- | --- | --- | GLU | 000 | 000 |
| Porcine | --- | --- | --- | --- | --- | VAL | 000 | THR |

FIG. 2b

| INHIBITORY ACTIVITY OF BCE CELL PROLIFERATION ||
| --- | --- |
| FRAGMENTS | ED50 (nM) |
| KRINGLE 1 | 320 |
| KRINGLE 2 | --- |
| KRINGLE 3 | 460 |
| KRINGLE 4 | --- |
| KRINGLE 5 | 0.300 |
| KRINGLES 2-3 | --- |
| KRINGLES 1-3 | 75 |
| KRINGLES 1-4 (ANGIOSTATIN) | 135 |

FIG. 4c

```
   1  CATCCTGGGA TTGGGACCCA CTTTCTGGGC ACTGCTGGCC AGTCCCAAAA
  51  TGGAACATAA GGAAGTGGTT CTTCTACTTC TTTTATTTCT GAAATCAGGT
 101  CAAGGAGAGC CTCTGGATGA CTATGTGAAT ACCCAGGGGG CTTCACTGTT
 151  CAGTGTCACT AAGAAGCAGC TGGGAGCAGG AAGTATAGAA GAATGTGCAG
 201  CAAAATGTGA GGAGGACGAA GAATTCACCT GCAGGGCATT CCAATATCAC
 251  AGTAAAGAGC AACAATGTGT GATAATGGCT GAAAACAGGA AGTCCTCCAT
 301  AATCATTAGG ATGAGAGATG TAGTTTTATT TGAAAAGAAA GTGTATCTCT
 351  CAGAGTGCAA GACTGGGAAT GGAAGAACT ACAGAGGGAC GATGTCCAAA
 401  ACAAAAAATG GCATCACCTG TCAAAAATGG AGTTCCACTT CTCCCCACAG
 451  ACCTAGATTC TCACCTGCTA CACACCCCTC AGAGGGACTG GAGGAGAACT
 501  ACTGCAGGAA TCCAGACAAC GATCCGCAGG GGCCCTGGTG CTATACTACT
 551  GATCCAGAAA AGAGATATGA CTACTGCGAC ATTCTTGAGT GTGAAGAGGA
 601  ATGTATGCAT TGCAGTGGAG AAAACTATGA CGGCAAAATT TCCAAGACCA
 651  TGTCTGGACT GGAATGCCAG GCCTGGGACT CTCAGAGCCC ACACGCTCAT
 701  GGATACATTC CTTCCAAATT TCCAAACAAG AACCTGAAGA AGAATTACTG
 751  TCGTAACCCC GATAGGGAGC TGCGGCCTTG GTGTTTCACC ACCGACCCCA
 801  ACAAGCGCTG GGAACTTTGT GACATCCCCC GCTGCACAAC ACCTCCACCA
 851  TCTTCTGGTC CCACCTACCA GTGTCTGAAG GGAACAGGTG AAAACTATCG
 901  CGGGAATGTG GCTGTTACCG TGTCCGGGCA CACCTGTCAG CACTGGAGTG
 951  CACAGACCCC TCACACACAT AACAGGACAC CAGAAAACTT CCCCTGCAAA
1001  AATTTGGATG AAAACTACTG CCGCAATCCT GACGGAAAAA GGGCCCCATG
1051  GTGCCATACA ACCAACAGCC AAGTGCGGTG GGAGTACTGT AAGATACCGT
1101  CCTGTGACTC CTCCCCAGTA TCCACGGAAC AATTGGCTCC CACAGCACCA
1151  CCTGAGCTAA CCCCTGTGGT CCAGGACTGC TACCATGGTG ATGGACAGAG
1201  CTACCGAGGC ACATCCTCCA CCACCACCAC AGGAAAGAAG TGTCAGTCTT
1251  GGTCATCTAT GACACCACAC CGGCACCAGA AGACCCCAGA AAACTACCCA
```
(SEQ ID NO:12)

FIG.6a

| | | | | |
|---|---|---|---|---|
|1301|AATGCTGGCC|TGACAATGAA|CTACTGCAGG·|AATCCAGATG|CCGATAAAGG|
|1351|CCCCTGGTGT|TTTACCACAG|ACCCCAGCGT|CAGGTGGGAG|TACTGCAACC|
|1401|TGAAAAAATG|CTCAGGAACA|GAAGCGAGTG|TTGTAGCACC|TCCGCCTGTT|
|1451|GTCCTGCTTC|CAGATGTAGA|GACTCCTTCC|GAAGAAGACT|GTATGTTTGG|
|1501|GAATGGGAAA|GGATACCGAG|GCAAGAGGGC|GACCACTGTT|ACTGGGACGC|
|1551|CATGCCAGGA|CTGGGCTGCC|CAGGAGCCCC|ATAGACACAG|CATTTTCACT|
|1601|CCAGAGACAA|ATCCACGGGC|GGGTCTGGAA|AAAAATTACT|GCCGTAACCC|
|1651|TGATGGTGAT|GTAGGTGGTC|CCTGGTGCTA|CACGACAAAT|CCAAGAAAAC|
|1701|TTTACGACTA|CTGTGATGTC|CCTCAGTGTG|CGGCCCCTTC|ATTTGATTGT|
|1751|GGGAAGCCTC|AAGTGGAGCC|GAAGAAATGT|CCTGGAAGGG|TTGTAGGGGG|
|1801|GTGTGTGGCC|CACCCACATT|CCTGGCCCTG|GCAAGTCAGT|CTTAGAACAA|
|1851|GGTTTGGAAT|GCACTTCTGT|GGAGGCACCT|TGATATCCCC|AGAGTGGGTG|
|1901|TTGACTGCTG|CCCACTGCTT|GGAGAAGTCC|CCAAGGCCTT|CATCCTACAA|
|1951|GGTCATCCTG|GGTGCACACC|AAGAAGTGAA|TCTCGAACCG|CATGTTCAGG|
|2001|AAATAGAAGT|GTCTAGGCTG|TTCTTGGAGC|CCACACGAAA|AGATATTGCC|
|2051|TTGCTAAAGC|TAAGCAGTCC|TGCCGTCATC|ACTGACAAAG|TAATCCCAGC|
|2101|TTGTCTGCCA|TCCCCAAATT|ATGTGGTCGC|TGACCGGACC|GAATGTTTCG|
|2151|TCACTGGCTG|GGGAGAAACC|CAAGGTACTT|TTGGAGCTGG|CCTTCTCAAG|
|2201|GAAGCCCAGC|TCCCTGTGAT|TGAGAATAAA|GTGTGCAATC|GCTATGAGTT|
|2251|TCTGAATGGA|AGAGTCCAAT|CCACCGAACT|CTGTGCTGGG|CATTTGGCCG|
|2301|GAGGCACTGA|CAGTTGCCAG|GGTGACAGTG|GAGGTCCTCT|GGTTTGCTTC|
|2351|GAGAAGGACA|AATACATTTT|ACAAGGAGTC|ACTTCTTGGG|GTCTTGGCTG|
|2401|TGCACGCCCC|AATAAGCCTG|GTGTCTATGT|TCGTGTTTCA|AGGTTTGTTA|
|2451|CTTGGATTGA|GGGAGTGATG|AGAAATAATT|AATTGGACGG|GAGACAG|

FIG.6b

ANTIANGIOGENIC PEPTIDES AND METHODS FOR INHIBITING ANGIOGENESIS

This application is a continuation-in-part of U.S. patent application Ser. No. 08/643219 filed May 3, 1996, now U.S. Pat. No. 5,801,146.

TECHNICAL FIELD

The present invention relates to the field of peptide chemistry. More particularly, the invention relates to the preparation and use of peptides containing amino acid sequences substantially similiar to the corresponding sequences of the kringle 5 region of mammalian plasminogen, pharmaceutical compositions containing the peptides, antibodies specific for the angiostatin receptor, means for angiostatin detection and measurement, cytotoxic agents linked to angiostatin proteins and treatment of diseases which arise from or are exacerbated by angiogenesis.

BACKGROUND OF THE INVENTION

Angiogenesis, the process by which new blood vessels are formed, is essential for normal body activities including reproduction, development and wound repair. Although the process is not completely understood, it is believed to involve a complex interplay of molecules which regulate the growth of endothelial cells (the primary cells of capillary blood vessels). Under normal conditions, these molecules appear to maintain the microvasculature in a quiescent state (i.e. one of no capillary growth) for prolonged periods which may last for as long as weeks or, in some cases, decades. When necessary (such as during wound repair), these same cells can undergo rapid proliferation and turnover within a 5 day period (Folkman, J. and Shing, Y., *The Journal of Biological Chemistry*, 267 (16), 10931–10934, and Folkman, J. and Klagsbrun, M., *Science*, 235, 442–447 (1987).

Although angiogenesis is a highly regulated process under normal conditions, many diseases (characterized as angiogenic diseases) are driven by persistent unregulated angiogenesis. Otherwise stated, unregulated angiogenesis may either cause a particular disease directly or exaserbate an existing pathological condition. For example, ocular neovacularization has been implicated as the most common cause of blindness and dominates approximately 20 eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of solid tumors are also dependent on angiogenesis (Folkman, J., *Cancer Research*, 46, 467–473 (1986), Folkman, J., *Journal of the National Cancer Institute*, 82, 4–6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., *The New England Journal of Medicine*, 324 (1), 1–8 (1991).

To date, several naturally occurring angiogenic factors have been described and characterized (Fidler, J. I. and Ellis, L. M., *Cell*, 79, 185–189 (1994). Recently, O'Reilly, et al. have isolated and purified a 38 kilodalton (kDa) protein from serum and urine of tumor-bearing mice that inhibits endothelial cell proliferation (O'Reilly, M. et al., *Cell*, 79, 315–328 (1994) and International Application WO 95/29242, published Nov. 2, 1995. Microsequence analysis of this endothelial inhibitor showed 98% sequence homology to an internal fragment of murine plasminogen. Angiostatin, as the murine inhibitory fragment was named, was a peptide which included the first four kringle regions of murine plasminogen. A peptide fragment from the same region of human plasminogen (i.e. containing kringles 1–4) also strongly inhibited proliferation of capillary endothelial cells in vitro and in vivo. The intact plasminogen from which this peptide fragment was derived did not possess as potent an inhibitory effect.

Several angiogenesis inhibitors are currently under development for use in treating angiogenic diseases (Gasparini, G. and Harris, A. L., *J. Clin. Oncol.*, 13 (3): 765–782, (1995), but there are disadvantages associated with these compounds. Suramin, for example, is a potent angiogenesis inhibitor but causes severe systemic toxicity in humans at doses required for antitumor activity. Compounds such as retinoids, interferons and antiestrogens are safe for human use but have weak antiangiogenic effects.

Thus, there is a need for compounds useful in treating angiogenic diseases in mammals. More specifically, there is a need for angiogenesis inhibitors which are safe for therapeutic use and which exhibit selective toxicity with respect to the pathological condition such as by selectively inhibiting the proliferation of cancer cells while exhibiting no or a low degree of toxicity to normal (ie. non-cancerous) cells. Such compounds should also be easily and cost-effectively made.

SUMMARY OF THE INVENTION

In its principle embodiment, the present invention provides a kringle 5 peptide fragment represented by the structural formula A-B-C-X-Y (I), or a pharmaceutically acceptable salt thereof, wherein A is absent or a nitrogen protecting group;

Y is absent or a carboxylic acid protecting group;

B is absent, a naturally-occuring amino acid residue or a peptide of between 2 and 197 amino acids (inclusive), the α-N-terminal optionally capped with A, the α-C-terminal optionally capped with Y and a substantial sequence homology to the corresponding amino acid sequence from $Asp^{334}$ to $Arg^{530}$ (inclusive) of SEQ ID NO: 1;

C is absent or $R^1$-$R^2$-$R^3$-$R^4$ wherein $R^1$ is lysyl, $R^2$ is selected from leucyl and arginyl, $R^3$ is selected from tyrosyl, 3-I-tyrosyl and phenylalanyl and $R^4$ is aspartyl, with the proviso that at least one of B or C is present, and X is absent, a naturally occuring amino acid residue or a peptide of between 2 and 11 amino acids (inclusive), the α-N-terminal optionally capped with A, the α-C-terminal optionally capped with Y and a substantial sequence homology to the corresponding amino acid sequence beginning at $Tyr^{535}$ and ending at $Phe^{546}$ of SEQ ID NO: 1.

The present invention also includes a method for treating a patient in need of antiangiogenesis therapy comprising administering to the patient a compound containing a kringle 5 peptide fragment.

The present invention also includes a composition for treating a patient in need of anti-angiogenesis therapy comprising a compound containing a kringle 5 peptide fragment, kringle 5 antisera, kringle 5 receptor agonists and antagonists and kringle 5 antagonists linked to cytotoxic agents either alone or in combination with a pharmaceutically acceptable excipient and/or optionally sustained release compounds to form a therapeutic composition.

The present invention also includes a composition for the treatment of a disease selected from the group consisting of cancer, arthritis, macular degeneration and diabetic retinopathy comprising a compound containing a kringle 5 peptide fragment.

The present invention also includes a composition comprising an isolated single or double-stranded polynucleotide sequence that encodes a kringle 5 peptide fragment or kringle 5 peptide fragment conjugate. Such a polynucleotide is preferably a DNA molecule. The present invention also includes a vector containing a DNA sequence encoding a kringle 5 peptide fragment or kringle 5 peptide fragment conjugate wherein the vector is capable of expressing a kringle 5 peptide fragment or kringle 5 peptide conjugate when present in a cell and a composition comprising a cell containing a vector wherein the vector contains a DNA sequence encoding a kringle 5 peptide fragment or kringle 5 peptide conjugate. The present invention further encompasses gene therapy methods whereby DNA sequences encoding a kringle 5 peptide fragment or kringle 5 peptide fragment conjugate are introduced into a patient to modify in vivo kringle 5 levels.

The present invention also includes a method of making a kringle 5 peptide fragment comprising the steps of: (a) exposing mammalian plasminogen to human or porcine elastase at a ratio of about 1:100 to about 1:300 to form a mixture of said plasminogen and said elastase; (b) incubating said mixture and (c) isolating the kringle 5 peptide fragment from said mixture.

The present invention also includes a method of making a kringle 5 peptide fragment comprising the steps of: (a) exposing mammalian plasminogen to human or porcine elastase at an elastase:plasminogen ratio of about 1:100 to about 1:300 to form a mixture of said elastase and said plasminogen; (b) incubating said mixture; and (c) isolating a protein conjugate of a kringle 5 peptide fragment from said mixture; (d) exposing said protein conjugate of the kringle 5 peptide fragment to pepsin at a ratio of about 1:0.2 to form a mixture of said pepsin and said plasminogen and (d) isolating said kringle 5 peptide fragment from said mixture.

The present invention also includes antibodies specific for the kringle 5 binding site and methods for the production of antibodies specific for the kringle 5 binding site. Antibodies can be monoclonal and polyclonal and can be used in diagnostic kits for detection and measurement of kringle 5 peptide fragment concentrations and for localization of kringle 5 proteins in tissues and cells. The antibodies specific for kringle 5 can be used in the diagnostic kits to detect the presence and quantity of kringle 5 peptide fragments which are indicative of diseases caused or exacerbated by angiogenesis, to isolate pure kringle 5 peptide fragments from mixtures containing kringle 5 peptide fragments and to isolate the kringle 5 receptor.

The present invention also includes methods and kits for the detection and measurement of kringle 5 peptide fragments in body fluid or tissue. The diagnostic kit would be in any configuration well-known to those of ordinary skill in the art and would provide instructions and the necessary kringle 5 peptide fragments and antisera for the measurement of kringle 5 peptide fragments in biological fluids and tissue extracts of animals and humans with and without tumors.

The present invention also includes a method for preparing kringle 5 peptide fragments or prodrugs of kringle 5 peptide fragments synthetically by standard methods of solid phase or solution phase chemistry or recombinant technology known to those of ordinary skill in the art.

The present invention also includes kringle 5 peptide fragments which can be labeled isotopically or with other molecules or proteins for use in the detection and visualization of kringle 5 binding sites with techniques including, but not limited to, radioimmunoassays, competitive and noncompetitive assays, bioluminescence and enzyme-linked immunoabsorbent assays.

BRIEF DESCRIPTION OF THE FIGURES

FIG. 1 shows the amino acid sequence of human plasminogen (SEQ ID NO: 1).

FIG. 2 shows the comparative homology in amino acid sequences of human (SEQ ID NO: 2), mouse (SEQ ID NO: 8), monkey (SEQ ID NO: 9), bovine (SEQ ID NO: 10), and porcine (SEQ ID NO: 11) kringle 5.

FIG. 4(c) shows a summary of $ED_{50}$ values obtained from the inhibition of various kringle fragments on BCE cell proliferation in vitro. In this Figure: kringle 1 represents the sequence of FIG. 1 from amino acid position 80 to amino acid position 163, kringle 2* represents the sequence of FIG. 1 from amino acid position 161 to amino acid position 245, kringle 3* represents the sequence of FIG. 1 from amino acid position 253 to amino acid position 335, kringle 4 represents the sequence of FIG. 1 from amino acid position 354 to amino acid position 443, kringles 2–3* represents the sequence of FIG. 1 from amino acid position 161 to amino acid position 335, kringles 1–3 represent the sequence of FIG. 1 from amino acid position 80 to amino acid position 353, kringles 1–4 represent the sequence of FIG. 1 from amino acid position 80 to amino acid position 443, and kringle 5 represents SEQ ID NO: 3.

* =Marti, D., et al., Eur, J. Biochem., 219: 455–462 (1994).

Figure 3:
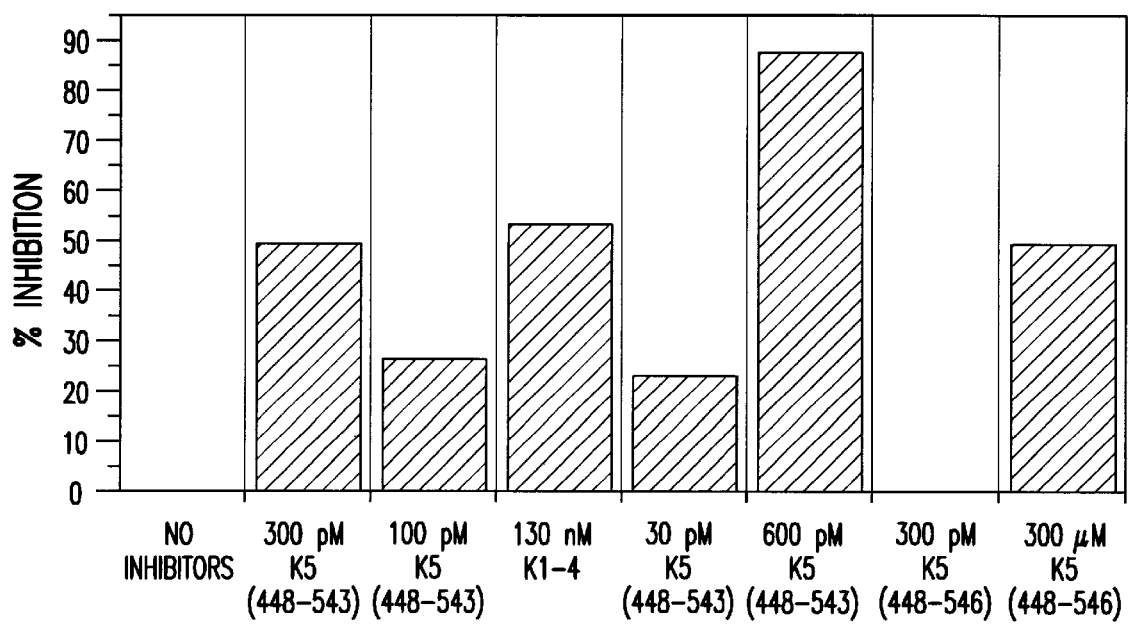
FIG. 3 shows a graph of the anti-proliferative activity of a single dose of various kringle fragments on bovine capillary endothelial (BCE) cells when tested in an in vitro cell proliferation assay.
Figure 4A:
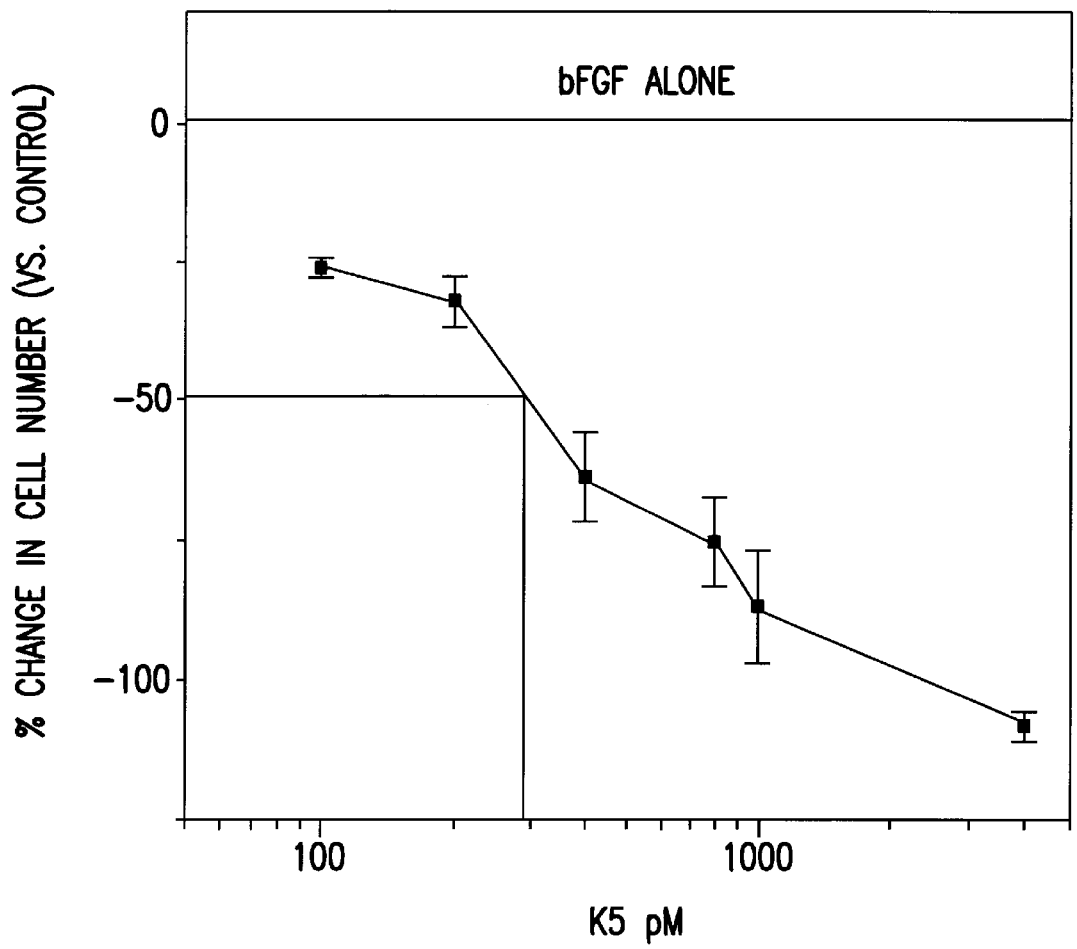
FIG. 4(a) shows a graph of the anti-proliferative activity of various concentrations of kringle 5 (SEQ ID NO: 3) on (BCE) cells when tested in an in vitro cell proliferation assay.
Figure 4B:
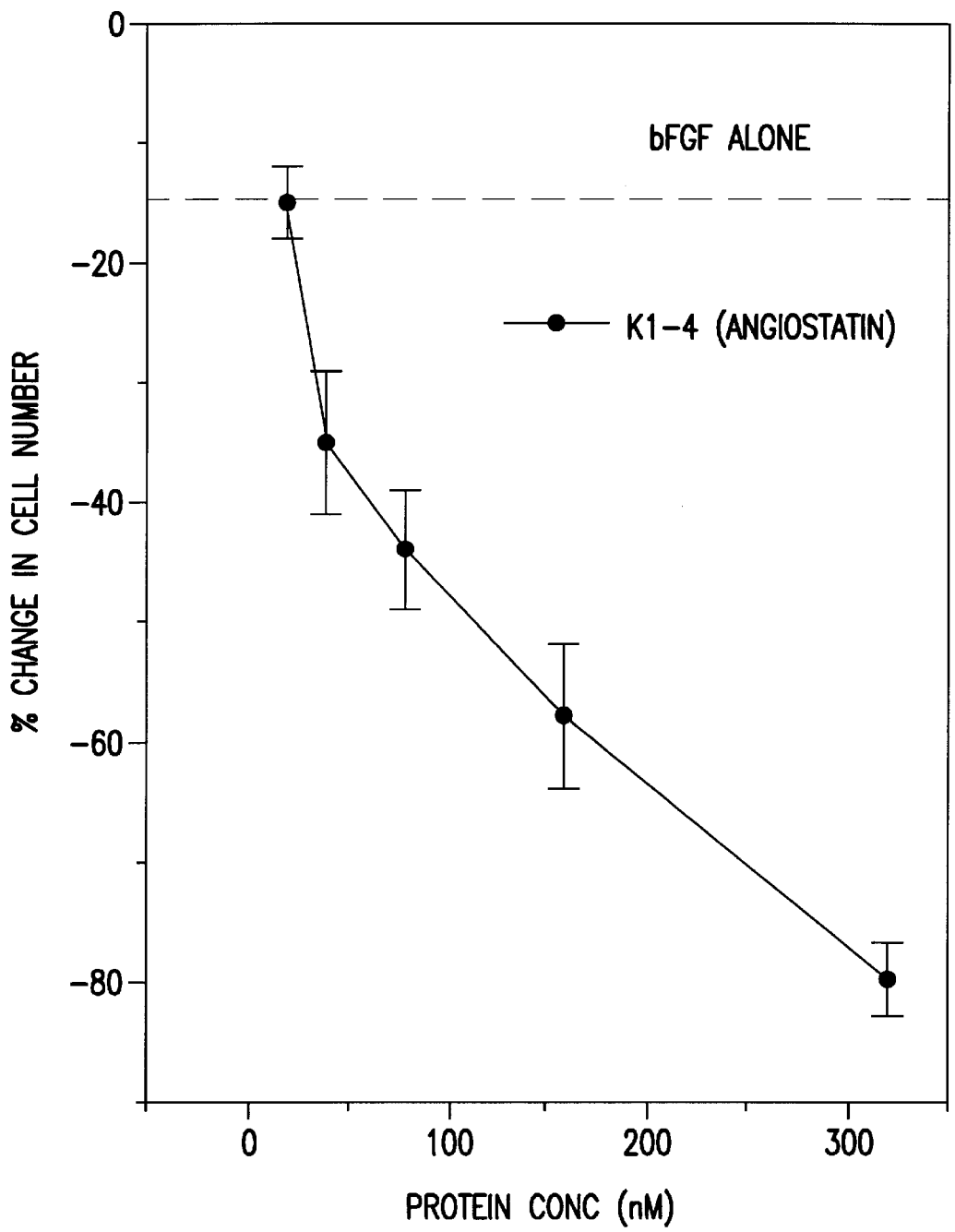
FIG. 4(b) shows a graph of the anti-proliferative activity of various concentrations of kringles 1–4 on BCE cells when tested in an in vitro cell proliferation assay.
Figure 5:
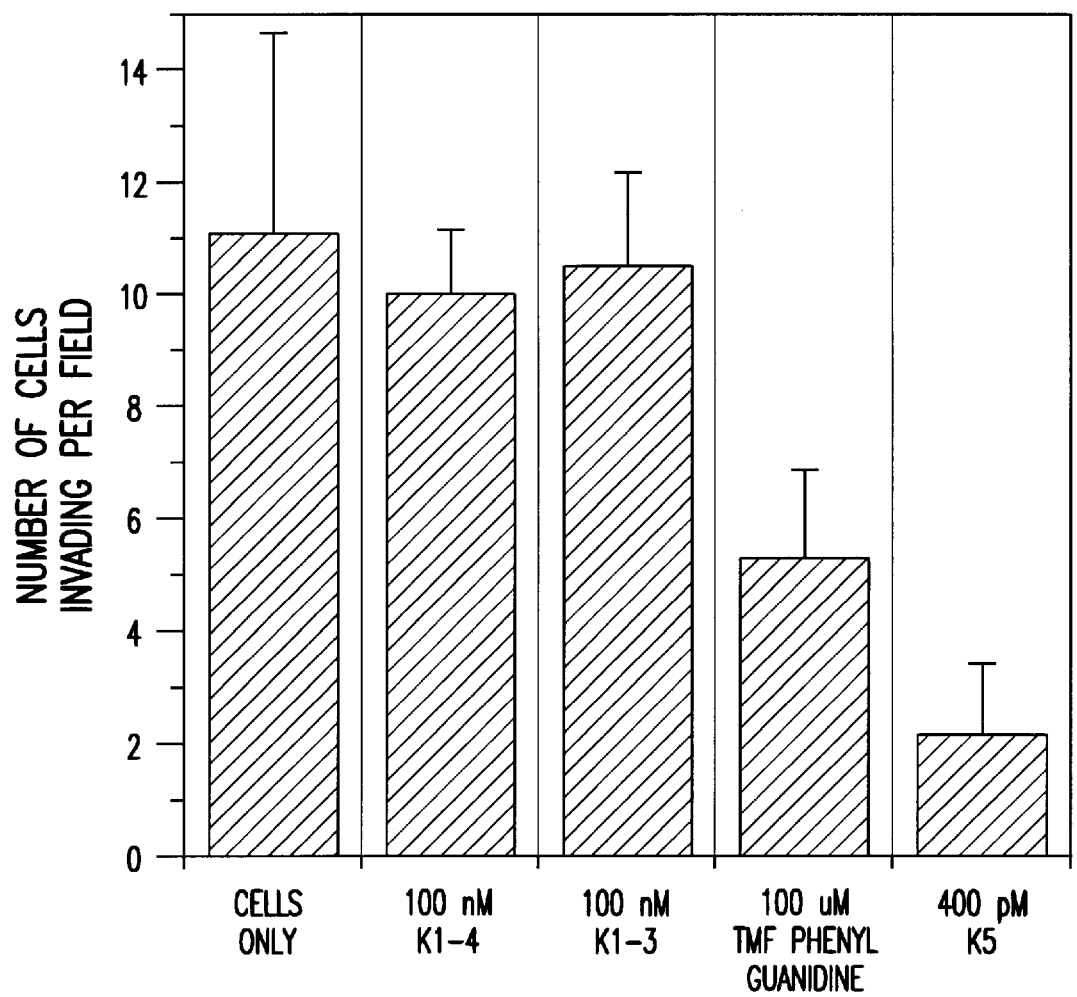

FIG. 5 shows a graph of the effect of various kringle fragments on inhibition of endothlial cell migration in vitro.

FIGS. 6(a)–6(b) shows the DNA sequence (SEQ ID NO: 12) of human plasminogen.

DETAILED DESCRIPTION OF THE INVENTION

As used herein, the term "kringle 5" refers to the region of mammalian plasminogen having three disulfide bonds which contribute to the specific three-dimensional confirmation defined by the fifth kringle region of the mammalian plasminogen molecule. One such disulfide bond links the cysteine residues located at amino acid positions 462 and 541, a second links the cysteine residues located at amino acid positions 483 and 524 and a third links the cysteine residues located at amino acid positions 512 and 536. The amino acid sequence of a complete mammalian plasminogen molecule (the human plasminogen molecule), including its kringle 5 region, is shown in FIG. 1 (SEQ ID NO: 1).

As used herein, the term "kringle 5 peptide fragment" refers to a peptide of between 4 and 104 amino acids (inclusive) with a substantial sequence homology to the corresponding peptide fragment of mammalian plasminogen, an α-N-terminus at about amino acid position 443 of intact mammalian plasminogen and an α-C-terminus at about position 546. The total length of the a kringle 5 peptide fragment may vary depending upon the manner in which the kringle 5 peptide is obtained or may vary somewhat in sequence depending upon the species from which it is obtained. For example, certain forms of kringle 5 peptide fragments may be produced by proteolytic cleavage of glu-plasminogen, lys-plasminogen or miniplasminogen using the enzymes human or porcine elastase. When produced in this manner, the α-C-terminal of the peptide resides at about amino acid 543 of SEQ ID NO: 1, but the α-N-terminal amino acid may begin at amino acid position 443, 449 or 454. Thus, a kringle 5 peptide fragment resulting from human or porcine elastase digestion of glu-plasminogen, lys-plasminogen or miniplasminogen may have a total length of either 101 (SEQ ID NO: 2), 95 (SEQ ID NO: 3) or 90 (SEQ ID NO: 4) amino acids. A summary of these kringle 5 peptide fragments is shown in Table 1. When produced in the aforementioned manner, a pool of these three fragments is obtained wherein about 60% of the fragments have a length of 95 amino acids, about 35% of the fragments have the length of 101 amino acids and about 5% of the fragments have a length of 90 amino acids. If desired, these various fragments may be further purified by reverse phase HPLC, a technique well-known to those skilled in the art.

Alternatively, kringle 5 peptide fragments or kringle 5 peptide fragments bound to protein conjugates may be obtained by expression of a recombinant molecule comprising a polynucleotide having a sequence which encodes proteins having kringle 5 peptide fragment with an α-N terminal at amino acid position 443, 449 or 454 (preferably at position 443) and an α-C-terminal at amino acid position 543 and 546 (preferably at position 543) and then purifying the peptide product which is expressed (see Menhart, N., et al, *Biochemistry*, 32: 8799–8806 (1993). The DNA sequence of human plasminogen has been published (Browne, M. J. et al. *Fibrinolysis*, 5 (4): 257–260 (1991) and is shown in FIGS. 6(*a–b*) (SEQ ID NO: 12). A polynucleotide sequence encoding kringle 5 begins at about nucleotide position 1421 of SEQ ID NO: 12 and ends at about nucleotide position 1723. This method of making a kringle 5 peptide fragment employs conventional techniques of molecular biology, microbiology, recombinant DNA and immunology, all of which are within the skill of the art and fully explained in the literature. (See for example, "Molecular Cloning: A Laboratory Manual" Second Edition by Sambrook et al., Cold Spring Harbor Press, 1989. For example, the gene for a kringle 5 peptide fragment may be isolated from cells or tissues that express high levels of kringle 5 peptide fragments by (1) isolating messenger RNA from the tissue or cells, (2) using reverse transcriptase to generate the corresponding DNA sequence and (3) using the polymerase chain reaction (PCR) with the appropriate primers to amplify the DNA sequence coding for the active kringle 5 amino acid sequence. Furthermore, a polynucleotide encoding a kringle 5 peptide fragment may be cloned into any commercially available expression vector (such as pBR322, pUC vectors and the like) or expression/purification vectors (such as a GST fusion vector (Pharmacia, Piscataway, N.J.)) and then expressed in a suitable procaryotic, viral or eucaryotic host. Purification may then be achieved by conventional means or, in the case of a commercial expression/purification system, in accordance with manufacturer's instructions.

Kringle 5 peptide fragments may also be synthesized by standard methods of solid phase chemistry known to those of ordinary skill in the art For example kringle 5 peptide fragments may be synthesized by solid phase chemistry techniques following the procedures described by Steward and Young (Steward, J. M. and Young, J. D., *Solid Phase Peptide Synthesis*, 2nd Ed., Pierce Chemical Company, Rockford, Ill., (1984) using an Applied Biosystem synthesizer. Similarly, multiple fragments may be synthesized then linked together to form larger fragments. These synthetic peptide fragments can also be made with amino acid substitutions at specific locations to test for kringle 5 fragment-like activity in vitro and in vivo. For solid phase peptide synthesis, a summary of the many techniques may be found in J. M. Stewart and J. D. Young, *Solid Phase Peptide Synthesis*, W. H. Freeman Co. (San Francisco), 1963 and J. Meienhofer, *Hormonal Proteins and Peptides*, vol. 2, p. 46, Academic Press (New York), 1973. For classical solution synthesis see G. Schroder and K. Lupke, *The Peptides*, Vol. 1, Academic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of kringle 5 peptide fragments. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene- sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of α-C-terminal carboxy peptides is 4-hydroxymethylphenoxymethyl-copoly(styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris (dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. The preferred method for coupling to the deprotected 4 (2',4'-dimethoxyphenyl-Fmoc-aminomethyl)phenoxy-acetamidoethyl resin is is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art. In a preferred embodiment, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide is purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing. Molecular weights of these kringle 5 peptide fragments are determined using Fast Atom Bombardment (FAB) Mass Spectroscopy. Solid phase kringle 5 peptide fragment synthesis is illustrated in Examples 1 to 12.

Depending on how they are produced, kringle 5 peptide fragments may exist with or without the aformentioned disulfide bonds of the kringle 5 region of mammalian plasminogen or may exist with disulfide bonds forming a tertiary structure which differs from the tertiary structure found in native mammalian plasminogen (for example, disulfide bonds between $Cys^{462}$ and $Cys^{483}$, between $Cys^{512}$ and and between $Cys^{524}$ and $Cys^{536}$ and $Cys^{541}$. Kringle 5 peptide fragments produced by enzymatic cleavage of Glu-, Lys- or miniplasminogen with elastase and/or pepsin (enzymes which cleave at sites removed from the cysteine linkages) will contain the native tertiary kringle 5 protein structure; kringle 5 peptide fragments prepared by solid phase peptide synthesis may or may not contain cystyl amino acyl residues and kringle 5 peptide fragments prepared by expression may contain disulfide bonds at different positions than those found in kringle 5 peptide fragments produced by enzymatic cleavage.

As used herein, the term "conjugate of a kringle 5 peptide fragment" means a kringle 5 peptide fragment chemically coupled to another protein to form a conjugate. Examples of conjugates of kringle 5 peptide fragments include a kringle 5 peptide fragment coupled to albumin or to a peptide fragment from another kringle region of mammalian plasminogen. Molecular weights of conjugates of kringle 5 peptide fragments are between about 1,000 and about 25,000 kDa.

As used herein, the term "substantial sequence homology" means approximately 60% amino acid identity, desirably at least approximately 70% amino acid identity, more desirably approximately 80% amino acid identity and most desirably approximately 95% amino acid identity of the corresponding peptide sequence of human plasminogen. Because the amino acid sequence or the number of amino acids in a kringle 5 peptide fragment may vary from species to species or from the method of production, the total number of amino acids in a kringle 5 peptide fragment cannot, in some instances, be defined exactly. Given that these sequences are identical in at least 73% of their amino acids, it is to be understood that the amino acid sequence of a kringle 5 peptide fragment is substantially similar among species and that methods of production of kringle 5 peptide fragments provide kringle 5 peptide fragments with substantial sequence homology to the corresponding amino acid sequences of human plasminogen. FIG. 2 shows the amino acid sequence of a human kringle 5 peptide fragment having 95 amino acids (SEQ ID NO: 2) is in comparison with the sequences of kringle 5 fragments from murine (SEQ ID NO: 8), Rhesus monkey (SEQ ID NO: 9), bovine (SEQ ID NO: 10) and porcine (SEQ ID NO: 11) plasminogen.

Thus, the present invention contemplates amino acid residue sequences that have substantial sequence homology to the sequences set forth herein such that those sequences demonstrate like biological activity to disclosed kringle 5 peptide fragment sequences. It is well known in the art that modifications and changes can be made without substantially altering the biological function of that peptide. For example, alterations to kringle 5 peptide fragments may enhance the peptide's potency or stability to enzymatic breakdown. Such contemplated sequences include those analogous sequences characterized by a change in amino acid residue sequence or type wherein the change does not alter the fundamental nature and biological activity of the aforementioned kringle 5 peptide fragments.

A kringle 5 peptide fragment of the present invention may be characterized on the basis of potency when tested for its ability to inhibit the growth of bovine capillary (BCE) cells in vitro. The data in Table 1 illustrate that the kringle 5 peptide fragment SEQ ID NO: 3 has a 100-fold increase in activity (i.e. at inhibiting BCE cell proliferation) when compared to the kringle 5 peptide fragment SEQ ID NO: 6 and a 400-fold increase in activity when compared to kringle 14 peptide fragments.

As used herein, the term "α-N-terminal" refers to the free alpha-amino group of an amino acid in a peptide, and the term "α-C-terminal" refers to the free alpha-carboxylic acid terminus of an amino acid in a peptide.

All peptide sequences are written according to the generally accepted convention whereby the α-N-terminal amino acid residue is on the left and the α-C-terminal is on the right.

As used herein, the term "N-protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene, "Protective Groups In Organic Synthesis," (John Wiley & Sons, New York (1981)), which is hereby incorporated by reference. Additionally, protecting groups can be used as prodrugs which are readily cleaved in vivo, for example, by enzymatic hydrolysis, to release the biologically active parent. N-protecting groups comprise loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz). For example, lysine may be protected at the α-N-terminal by an acid labile group (e.g. Boc) and protected at the ε-N-terminal by a base labile group (e.g. Fmoc) then deprotected selectively during synthesis.

As used herein, the term "carboxy protecting group" refers to a carboxylic acid protecting ester or amide group employed to block or protect the carboxylic acid functionality while the reactions involving other functional sites of the compound are performed. Carboxy protecting groups are disclosed in Greene, "Protective Groups in Organic Synthesis" pp. 152–186 (1981), which is hereby incorporated by reference. Additionally, a carboxy protecting group can be used as a prodrug whereby the carboxy protecting group can be readily cleaved in vivo, for example by enzymatic hydrolysis, to release the biologically active parent Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$–$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl) alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

Representative amide carboxy protecting groups are aminocarbonyl and loweralkylaminocarbonyl groups.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester. Preferred amide carboxy protecting groups are loweralkylaminocarbonyl groups. For example, aspartic acid may be protected at the α-C-terminal by an acid labile group (e.g. t-butyl) and protected at the β-C-terminal by a hydrogenation labile group (e.g. benzyl) then deprotected selectively during synthesis.

As used herein, the term "loweralkylaminocarbonyl" means a —C(O)NHR$^{10}$ group which caps the α-C-terminal of a synthetic, kringle 5 peptide fragment wherein R$^{10}$ is $C_1$–$C_4$ alkyl.

As used herein, the term "aminocarbonyl" indicates a —C(O)NH$_2$ group which caps the α-C-terminal of a synthetic, kringle 5 peptide fragment.

As used herein, the term "prodrug" refers to compounds which are rapidly transformed in vivo to yield the parent compound, for example, by enzymatic hydrolysis in blood. A thorough discussion is provided in T. Higuchi and V. Stella, *Prodrugs as Novel Delivery Systems,* Vol. 14 of the A.C.S. Symposium Series and in Edward B. Roche, ed., *Bioreversible Carriers in Drug Design,* American Pharmaceutical Association and Permagon Press, 1987.

As used herein, the term "pharmaceutically acceptable prodrug" refers to (1) those prodrugs of the compounds of the present invention which are, within the scope of sound medical judgement, suitable for use in contact with the tissues of humans and lower animals without undue toxicity, irritation, allergic response and the like, commensurate with a suitable benefit-to-risk ratio and effective for their intended use and (2) zwitterionic forms, where possible, of the parent compound.

As used herein, the term "antiangiogenesis activity" refers to the capability of a molecule to inhibit the growth of blood vessels.

As used herein, the term "endothelial inhibiting activity" refers to the capability of a molecule to inhibit angiogenesis in general and, for example, to inhibit the growth or migration of bovine capillary endothelial cells in culture in the presence of fibroblast growth factor or other known growth factors.

As used herein, the term "ED$_{50}$" is an abbreviation for the dose of a kringle 5 peptide fragment which is effective to inhibit the growth of blood vessels or inhibit the growth of bovine capillary endothelial cells in culture in the presence of fibroblast growth factor or other known growth factors or inhibit the migration of endeothelial cells by one-half of what the growth or migration would be in the absence of the inhibitor.

As used herein, for the most part, the names of naturally-occuring amino acids and aminoacyl residues used herein follow the naming conventions suggested by the IUPAC Commission on the Nomenclature of Organic Chemistry and the IUPAC-IUB Commission on Biochemical Nomenclature as set out in *Nomenclature of α-Amino Acids (Recommendations,* 1974), Biochemistry, 14 (2), (1975). Accordingly, the terms "Ala," "Arg," "Asn," "Asp," "Cys," "Gln," "Glu," "Gly," "His," "Ile," "Leu," "Lys," "Met," "Phe," "Pro," "Ser," "Thr," "Trp," "Tyr" and "Val" refer to the amino acids alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine and their corresponding aminoacyl residues in peptides in their L-, D- or D, L- forms. Where no specific configuration is indicated, one skilled in the art would understand that the stereochemistry of the α-carbon of the amino acids and aminoacyl residues in peptides described in this specification and the appended claims is the naturally occuring or "L" configuration with the exception of the achiral molecule glycine and with the further exception of any amino acids which are achiral or otherwise designated as "D-."

As used herein, the term "3-I-Tyr" means a L-, D-, or D, L-tyrosyl residue wherein a hydrogen radical ortho to the phenolic hydroxyl is replaced by an iodide radical. The iodide radical may be radioactive or nonradioactive.

The present invention also contemplates amino acid residues with non-naturally occuring side chain residues such as homophenylalanine, phenylglycine, norvaline, norleucine, ornithine, thiazoylalanine (2-, 4- and 5- substituted) and the like.

Thus, it is to be understood that the present invention is contemplated to encompass any derivatives of kringle 5 peptide fragments which have antiangiogenic activity and includes the entire class of kringle 5 peptide fragments described herein and derivatives of those kringle 5 peptide fragments. Additionally, the invention is not dependent on the manner in which the kringle 5 peptide fragment is produced, i.e. by (1) proteolytic cleavage of an isolated mammalian plasminogen, (2) by expression of a recombinant molecule having a polynucleotide which encodes the amino acid sequence of a kringle 5 peptide fragment or a conjugate containing a kringle 5 peptide fragment and (3) solid phase synthetic techniques known to those of ordinary skill in the art.

In one embodiment, the present invention provides peptides with the general structure B-C-X wherein B is a 88-mer peptide beginning at Val$^{443}$ and ending at Arg$^{530}$ of SEQ ID NO: 1; C, R$^1$ and R$^4$ are previously defined, R$^2$ is leucyl; R$^3$ is tyrosyl and X is a 9-mer peptide beginning at Tyr$^{535}$ and ending at Ala$^{543}$ of SEQ ID NO: 1 (SEQ ID NO: 2).

In another embodiment, the present invention provides peptides with the general structure B-C-X wherein B is a 82-mer peptide beginning at Val$^{449}$ and ending at Arg$^{530}$ of SEQ ID NO: 1; C, R$^1$ and R$^4$ are previously defined; R$^2$ is leucyl; R$^3$ is tyrosyl and X is a 9-mer peptide beginning at Tyr$^{535}$ and ending at Ala$^{543}$ of SEQ ID NO: 1 (SEQ ID NO: 3).

In yet another embodiment, the present invention provides peptides with the general structure B-C-X wherein B is a 77-mer peptide beginning at Val$^{454}$ and ending at Arg$^{530}$ of SEQ ID NO: 1; C, R$^1$ and R$^4$ are previously defined; R$^2$ is leucyl; R$^3$ is tyrosyl and X is a 9-mer peptide beginning at Tyr$^{535}$ and ending at Ala$^{543}$ of SEQ ID NO: 1 (SEQ ID NO: 4).

In yet another embodiment, the present invention provides peptides with the general structure B-C-X wherein B is a 88-mer peptide beginning at Val$^{443}$ and ending at Arg$^{530}$ of SEQ ID NO: 1; C, R$^1$ and R$^4$ are previously defined; R$^2$ is leucyl; R$^3$ is tyrosyl and X is a 12-mer peptide beginning at Tyr$^{535}$ and ending at Phe$^{546}$ of SEQ ID NO: 1 (SEQ ID NO: 5).

In yet another embodiment, the present invention provides peptides with the general structure structure B-C-X wherein B is a 82-mer peptide beginning at Val$^{449}$ and ending at Arg$^{530}$ of SEQ ID NO: 1; C, R$^1$ and R$^4$ are previously defined; R$^2$ is leucyl; R$^3$ is tyrosyl and X is a 12-mer peptide beginning at Tyr$^{535}$ and ending at Phe$^{546}$ of SEQ ID NO: 1 (SEQ ID NO: 6).

In yet another embodiment, the present invention provides peptides with the general structure B-C-X wherein B is a 77-mer peptide beginning at Val$^{454}$ and ending at Arg$^{530}$ of SEQ ID NO: 1; C, R$^1$ and R$^4$ are previously defined; R$^2$ is leucyl, R$^3$ is tyrosyl and X is a 12-mer peptide beginning at Tyr$^{535}$ and ending at Phe$^{546}$ of SEQ ID NO: 1 (SEQ ID NO: 7).

In yet another embodiment, the present invention provides peptides with the general structure B-C-X wherein B is a 176-mer peptide beginning at Val$^{355}$ and ending at Arg$^{530}$ of SEQ ID NO: 1; C, R$^1$ and R$^4$ are previously defined; R$^2$ is leucyl, R$^3$ is tyrosyl and X is a 12-mer peptide beginning at Tyr$^{535}$ and ending at Ala$^{543}$ of SEQ ID NO: 1.

In yet another embodiment, the present invention provides peptides with the general structure B-C-X wherein B is a 176-mer peptide beginning at Val$^{355}$ and ending at Arg$^{530}$ of SEQ ID NO: 1; C, R$^1$ and R$^4$ are previously defined; R$^2$ is leucyl, R$^3$ is tyrosyl and X is a 12-mer peptide beginning at Tyr$^{535}$ and ending at Phe$^{546}$ of SEQ ID NO: 1.

In yet another embodiment, the present invention provides peptides with the general structure A-B-Y wherein A is acetyl, B is a 13-mer peptide beginning at amino acid Val$^{449}$ and ending at Asp$^{461}$ of SEQ ID NO: 1 and Y is aminocarbonyl.

In yet another embodiment, the present invention provides peptides with the general structure A-B-Y wherein A is acetyl, B is a 20-mer peptide beginning at amino acid Met$^{463}$ and ending at Pro$^{482}$ of SEQ ID NO: 1 and Y is aminocarbonyl.

In yet another embodiment, the present invention provides peptides with the general structure A-B-Y wherein A is acetyl, B is a 28-mer peptide beginning at amino acid Gln$^{484}$ and ending at amino acid Tyr$^{511}$ of SEQ ID NO: 1 and Y is aminocarbonyl.

In yet another embodiment, the present invention provides peptides with the general structure A-B-Y wherein A is acetyl; B is an 11-mer peptide beginning at amino acid position Arg$^{513}$ and ending at amino acid position Trp$^{523}$ of SEQ ID NO: 1 and Y is aminocarbonyl.

In yet another embodiment, the present invention provides peptides with the general structure A-B-C-Y wherein A is acetyl; B is a dipeptide beginning at amino acid position Pro$^{529}$ and ending at amino acid position Arg$^{530}$ of SEQ ID NO: 1; C, R$^1$ and R$^4$ are previously defined; R$^2$ is leucyl; R$^3$ is tyrosyl and Y is aminocarbonyl.

In yet another embodiment, the present invention provides peptides with the general structure A-B-C-Y wherein A is acetyl; B is a dipeptide beginning at amino acid position Pro$^{529}$ and ending at amino acid position Arg$^{530}$ of SEQ ID NO: 1; C, R$^1$ and R$^4$ are previously defined; R$^2$ is leucyl; R$^3$ is tyrosyl and Y is aminocarbonyl.

In yet another embodiment, the present invention provides peptides with the general structure A-B-C-X-Y wherein A is acetyl; B is a hexapeptide beginning at amino acid position Tyr$^{525}$ and ending at amino acid position Arg$^{530}$ of SEQ ID NO: 1; C, R$^1$ and R$^4$ are previously defined; R$^2$ is leucyl, R$^3$ is tyrosyl, X is tyrosyl and Y is aminocarbonyl.

In yet another embodiment, the present invention provides peptides with the general structure A-B-C-X-Y wherein A is acetyl; B is arginyl; C, R$^1$ and R$^4$ are previously defined; R$^2$ is leucyl; R$^3$ is tyrosyl; X is tyrosyl and Y is aminocarbonyl.

In yet another embodiment, the present invention provides peptides with the general structure A-B-C-X-Y wherein A is acetyl, B is a dipeptide beginning at amino acid position Pro$^{529}$ and ending at amino acid position Arg$^{530}$ of SEQ ID NO: 1; C, R$^1$ and R$^4$ are previously defined; R$^2$ is leucyl; R$^3$ is tyrosyl; X is 3-I-tyrosyl and Y is aminocarbonyl.

In yet another embodiment, the present invention provides peptides with the general structure A-B-C-X-Y wherein A is acetyl, B is a dipeptide beginning at amino acid position Pro$^{529}$ and ending at amino acid position Arg$^{530}$ of SEQ ID NO: 1; C, R$^1$ and R$^4$ are previously defined; R$^2$ is leucyl; R$^3$ is 3-I-tyrosyl; X is tyrosyl and Y is aminocarbonyl.

In yet another embodiment, the present invention provides peptides with the general structure A-C-Y wherein A is acetyl; C, R$^1$ and R$^4$ are previously defined; R$^2$ is leucyl, R$^3$ is tyrosyl, X is tyrosyl and Y is aminocarbonyl.

Representative compounds of formula (I) include:

H$_2$N-Val$^{443}$-Ala$^{543}$-CO$_2$H of SEQ ID NO: 1 (SEQ ID NO: 2)
H$_2$N-Val$^{449}$-Ala$^{543}$-CO$_2$H of SEQ ID NO: 1 (SEQ ID NO: 3)
H$_2$N-Val$^{454}$-Ala$^{543}$-CO$_2$H of SEQ ID NO: 1 (SEQ ID NO: 4)
H$_2$N-Val$^{443}$-Phe$^{546}$-CO$_2$H of SEQ ID NO: 1 (SEQ ID NO: 5)
H$_2$N-Val$^{449}$-Phe$^{546}$-CO$_2$H of SEQ ID NO: 1 (SEQ ID NO: 6)
H$_2$N-Val$^{454}$-Phe$^{546}$-CO$_2$H of SEQ ID NO: 1 (SEQ ID NO: 7)
N-Ac-Val$^{449}$-Asp$^{461}$-NH$_2$ of SEQ ID NO: 1
N-Ac-Met$^{463}$-Pro$^{482}$-NH$_2$ of SEQ ID NO: 1
N-Ac-Gln$^{484}$-Tyr$^{511}$-NH$_2$ of SEQ ID NO: 1
N-Ac-Arg$^{513}$-Trp$^{523}$-NH$_2$ of SEQ ID NO: 1
N-Ac-Tyr$^{525}$-Tyr$^{535}$-NH$_2$ of SEQ ID NO: 1
N-Ac-Pro$^{529}$-Tyr$^{535}$-NH$_2$ of SEQ ID NO: 1
N-Ac-Pro$^{529}$-Asp$^{534}$-NH$_2$ of SEQ ID NO: 1
N-Ac-Arg$^{530}$-Tyr$^{535}$-NH$_2$ of SEQ ID NO: 1
N-Ac-Pro-Arg-Lys-Leu-Tyr-Asp-3-I-Tyr-NH$_2$ (SEQ ID NO: 13)
N-Ac-Pro-Arg-Lys-Leu-3-I-Tyr-Asp-Tyr-NH$_2$ (SEQ ID NO: 14)
N-Ac-H-Lys$^{531}$-Asp$^{534}$-NH$_2$ of SEQ ID NO: 1
H$_2$N-Val$^{355}$-Ala$^{543}$-CO$_2$H of SEQ ID NO: 1
H$_2$N-Val$^{355}$-Phe$^{546}$-CO$_2$H of SEQ ID NO: 1

The compounds of the invention, including but not limited to those specified in the examples, possess anti-angiogenic activity. As angiogenesis inhibitors, such compounds are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas; prophylaxis of autoimmune diseases including rheumatoid, immune and degenerative arthritis; ocular diseases including diabetic retinopathy, retinopathy of prematurity, corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids) and diseases which have angiogenesis as a pathologic consequence including cat scratch disease (Rochele minalia quintosa) and ulcers (Helicobacter pylori). Another use is as a birth control agent which inhibits ovulation and establishment of the placenta.

The compounds of the present invention may also be useful for the prevention of metastases from the tumors described above either when used alone or in combination with radiotherapy and/or other chemotherapeutic treatments conventionally administered to patients for treating angiogenic diseases. For example, when used in the treatment of solid tumors, compounds of the present invention may be administered with chemotherapeutic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogs including methotrexate; pyrimidine analogues including 5-fluorouracil, cytosine arabinoside; purine analogs including 6-mercaptopurine and 6-thioguanine; antitumor antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar. For example, a tumor may be treated conventionally with surgery, radiation or chemotherapy and kringle 5 administration with subsequent kringle 5 adminsteration to extend the dormancy of micrometastases and to stabilize and inhibit the growth of any residual primary tumor.

Cytotoxic agents such as ricin may be linked to kringle 5 peptide fragments and thereby provide a tool for destruction of cells that bind kringle 5. Peptides linked to cytotoxic agents may be infused in a manner designed to maximize delivery to the desired location. For example, ricin-linked high affinity kringle 5 fragments may be delivered via cannula directly into the target or into vessels supplying the target site. Such agents may also be delivered in a controlled manner through osmotic pumps coupled to infusion cannulae. A combination of kringle 5 antagonists may be co-applied with stimulators of angiogenesis to increase vascularization of tissue. Therapeutic regimens of this type could provide an effective means of destroying metastatic cancer.

The compounds of the present invention may be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences*, 1977, 66: 1 et seq., which is hereby incorporated herein by reference. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quarternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of kringle 5 peptide fragments by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic anines useful for the formation of base addition salts include ethylenediamine, ethanolamine, diethanolamine, piperidine, piperazine and the like. Preferred salts of the compounds of the invention include phosphate, tris and acetate.

Kringle 5 peptide fragments, kringle 5 antisera, kringle 5 receptor agonists, kringle 5 receptor antagonists or combinations thereof may be combined with pharmaceutically acceptable sustained-release matrices, such as biodegradable polymers, to form therapeutic compositions. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix is desirably chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Kringle 5 peptide fragments, kringle 5 receptor agonists, kringle 5 receptor antagonists or combinations thereof may be combined with pharmaceutically acceptable excipients or carriers to form therapeutic compositions. A pharmaceutically acceptable carrier or excipient refers to a non-toxic solid, semi-solid or liquid filler, diluent, encapsulating material or formulation auxiliary of any type. The compositions may be administered parenterally, sublingually, intracisternally, intravaginally, intraperitoneally, rectally, bucally or topically (as by powder, ointment, drops, transdermal patch or iontophoresis device).

The term "parenteral," as used herein, refers to modes of administration which include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly (orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

Topical administration includes administration to the skin, mucosa and surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers. For topical administration to the eye, a compound of the invention is delivered in a pharmaceutically acceptable ophthalmic vehicle such that the compound is maintained in contact with the ocular surface for a sufficient time period to allow the compound to penetrate the corneal and internal regions of the eye, as, for example, the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material. Alternatively, a compound of the invention may be injected directly into the vitrious and aqueous humor.

The composition may be pressurized and contain a compressed gas such as nitrogen or a liquified gas propellant. The liquified propellant medium and indeed the total composition is preferably such that the active ingredient does not dissolve therein to any substantial extent. The pressurized composition may also contain a surface active agent such as a liquid or solid non-ionic surface active agent or may be a solid anionic surface active agent. It is preferred to use the solid anionic surface active agent in the form of a sodium salt.

Compositions for rectal or vaginal administration are preferably suppositories which may be prepared by mixing the compounds of this invention with suitable non-irritating excipients or carriers such as cocoa butter, polyethylene glycol or a suppository wax which are solids at room temperature but liquids at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form may contain, in addition to a compound of the present invention, stabilizers, preservatives, excipients and the like. The preferred lipids are the phospholipids and the phosphatidyl cholines (lecithins), both natural and synthetic. Methods to form liposomes are known in the art. See, for example, Prescott, Ed., *Methods in Cell Biology,* Volume XIV, Academic Press, New York, N.Y. (1976), p. 33 et seq., which is hereby incorporated herein by reference.

When used in the above or other treatments, a therapeutically effective amount of one of the compounds of the present invention may be employed in pure form or, where such forms exist, in pharmaceutically acceptable salt form and with or without a pharmaceutically acceptible excipient. A "therapeutically effective amount" of the compound of the invention means a sufficient amount of the compound to treat an angiogenic disease (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidential with the specific compound employed and like factors well known in the medical arts. For example, it is well within the skill of the art to start doses of the compound at levels lower than those required to achieve the desired therapeutic effect and to gradually increase the dosage until the desired effect is achieved. Total daily dose of kringle 5 peptide fragments to be administered locally or systemically to a human or other mammal host in single or divided doses may be in amounts, for example, from 0.0001 to 200 mg/kg body weight daily and more usually 1 to 300 mg/kg body weight. If desired, the effective daily dose may be divided into multiple doses for purposes of administration. Consequently, single dose compositions may contain such amounts or submultiples thereof to make up the daily dose.

It will be understood that agents which can be combined with the compound of the present invention for the inhibition, treatment or prophylaxis of angiogenic diseases are not limited to those listed above, but include, in principle, any agents useful for the treatment or prophylaxis of angiogenic diseases.

The present invention also encompasses gene therapy whereby the gene encoding kringle 5 peptide fragments or kringle 5 peptide fragment conjugates is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12 (4): 335–356 (1992), which is hereby incorporated herein by reference. Gene therapy encompasses incorporation of DNA sequences into somatic cells or germ line cells for use in either ex vivo or in vivo therapy. Gene therapy functions to replace genes, to augment normal or abnormal gene function and to combat infectious diseases and other pathologies.

Strategies for treating medical problems with gene therapy include therapeutic strategies such as identifying the defective gene and then adding a functional gene to either replace the function of the defective gene or to augment a slightly functional gene or prophylactic strategies such as adding a gene which encodes a protein product that will treat the condition or that will make the tissue or organ more susceptible to a treatment regimen. As an example of a prophylactic strategy, a gene encoding a kringle 5 peptide fragment or a kringle 5 peptide fragment conjugate may be placed in a patient and thus prevent occurrence of angiogenesis or a gene that makes tumor cells more susceptible to radiation could be inserted so that radiation of the tumor would cause increased killing of the tumor cells.

Many protocols for the transfer of kringle 5 peptide fragment DNA or kringle 5 peptide fragment regulatory sequences are envisioned in this invention. Transfection of promoter sequences, other than ones specifically associated with a kringle 5 peptide fragment or other sequences which would increase production of kringle 5 peptide fragments, are also envisioned as methods of gene therapy. An example of this technology is found in Transkaryotic Therapies, Inc., of Cambridge, Mass., using homologous recombination to insert a "genetic switch" which turns on an erythropoietin gene in cells as disclosed in Genetic Engineering News, Apr. 15, 1994, which is hereby incorporated herein by reference. Such "genetic switches" could be used to activate a kringle 5 peptide fragment (or a kringle 5 receptor) in cells not normally expressing these proteins.

Gene transfer methods for gene therapy fall into three broad categories: (1) physical (e.g., electroporation, direct gene transfer and particle bombardment), (2) chemical (e.g. lipid-based carriers and other non-viral vectors) and (3) biological (e.g. virus derived vectors). For example, non-viral vectors such as liposomes coated with DNA may be directly injected intravenously into the patient It is believed that the liposome/DNA complexes are concentrated in the liver where they deliver the DNA to macrophages and Kupffer cells. Vectors or the "naked" DNA of the gene may also be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer and in vitro gene transfer. In ex vivo gene transfer, cells are taken from the patient and grown in cell culture. The DNA is transfected into the cells, and the transfected cells are expanded in number and then reimplanted in the patient. In in vitro gene transfer, the transformed cells are cells growing in culture, such as tissue culture cells, and not particular cells from a particular patient. These "laboratory cells" are transfected, and the transfected cells are selected and expanded for either implantation into a patient or for other uses. In vivo gene transfer involves introducing the DNA into the cells of the patient when the cells are within the patient All three of the broad based categories described above may be used to achieve gene transfer in vivo, ex vivo and in vitro.

Mechanical (i.e. physical) methods of DNA delivery can be achieved by microinjection of DNA into germ or somatic cells, pneumatically delivered DNA-coated particles such as the gold particles used in a "gene gun" and inorganic chemical approaches such as calcium phosphate transfection. It has been found that physical injection of plasmid DNA into muscle cells yields a high percentage of cells which are transfected and have a sustained expression of marker genes. The plasmid DNA may or may not integrate into the genome of the cells. Non-integration of the transfected DNA would allow the transfection and expression of gene product proteins in terminally differentiated, non-proliferative tissues for a prolonged period of time without fear of mutational insertions, deletions or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer may also be employed for injecting DNA into cells, tissues and organs. With a particle bombardment device, or "gene gun," a motive force is generated to accelerate DNA-coated high density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art Chemical methods of gene therapy involve carrier-mediated gene transfer through the use of fusogenic lipid vesicles such as liposomes or other vesicles for membrane fusion. A carrier harboring a DNA of interest can be conveniently introduced into body fluids or the bloodstream and then site specifically directed to the target organ or tissue in the body. Cell or organ-specific DNA-carrying liposomes, for example, can be developed and the foreign DNA carried by the liposome absorbed by those specific cells. Injection of immunoliposomes that are targeted to a specific receptor on certain cells can be used as a convenient method of inserting the DNA into the cells bearing that receptor. Another carrier system that has been used is the asialoglycoprotein/polylysine conjugate system for carrying DNA to hepatocytes for in vivo gene transfer.

Transfected DNA may also be complexed with other kinds of carriers so that the DNA is carried to the recipient cell and then deposited in the cytoplasm or in the nucleoplasm. DNA can be coupled to carrier nuclear proteins in specifically engineered vesicle complexes and carried directly into the nucleus.

Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Biological gene therapy methodologies employ viral vectors to insert genes into cells. The term "vector" as used herein means a carrier which may contain or associate with specific polynucleotide sequences and which functions to transport the specific polynucleotide sequences into a cell. The transfected cells may be cells derived from the patient's normal tissue, the patient's diseased tissue or non-patient cells. Examples of vectors include plasmids and infective microorganisms such as viruses or nonviral vectors such as the ligand-DNA conjugates, liposomes and the lipid-DNA complexes discussed above.

It may be desirable that a recombinant DNA molecule comprising a kringle 5 peptide fragment DNA sequence is operatively linked to an expression control sequence to form an expression vector capable of expressing a kringle 5 peptide fragment. Alternatively, gene regulation of kringle 5 peptide fragments may be accomplished by administering compounds that bind to the kringle 5 gene or control regions associated with the kringle 5 gene or its corresponding RNA transcript to modify the rate of transcription or translation.

Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA completed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome. For example, altered retrovirus vectors have been used in ex vivo methods to introduce genes into peripheral and tumor-infiltrating lymphocytes, hepatocytes, epidermal cells, myocytes or other somatic cells (which may then be introduced into the patient to provide the gene product from the inserted DNA).

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell-free virion so injection of producer cell lines are not necessary. Another potential advantage to adenoviral vectors is the ability to achieve long term expression of heterologous genes in vivo.

Viral vectors have also been used to insert genes into cells using in vivo protocols. To direct tissue-specific expression of foreign genes, cis-acting regulatory elements or promoters that are known to be tissue-specific may be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus-infected surrounding cells, in turn, also expressed the gene product. A viral vector can be delivered directly to the in vivo site (by catheter, for example) thus allowing only certain areas to be infected by the virus and providing long-term, site-specific gene expression. In vivo gene transfer using retrovirus vectors has also been demonstrated in mammary tissue and hepatic tissue by injection of the altered virus into blood vessels leading to the organs.

Kringle 5 peptide fragments may also be produced and used in a variety of applications. As examples, different peptide fragments of kringle 5 can be used (1) as agonists and antagonists active at kringle 5 binding sites, (2) as antigens for the development of specific antisera, (3) as peptides for use in diagnostic kits and (4) as peptides linked to or used in combination with cytotoxic agents for targeted killing of cells that bind kringle 5 peptide fragments. The amino acid sequences that comprise these peptide fragments may be selected on the basis of their position on the exterior regions of the molecule which are accessible for binding to antisera or the inhibitory potency of the peptide fragments toward processes arising from or exaserbated by angiogenesis. Furthermore, these peptide sequences may be compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules and thereby enhances the potential for high specificity in the development of antisera, agonists and antagonists to kringle 5.

Kringle 5 peptide fragments may also be used as a means to isolate a kringle 5 receptor by immobilization of the kringle 5 peptide fragment on a solid support in, for example, an affinity column through which cultured endothelial cells or membrane extracts are passed. As is known in the art, isolation and purification of a kringle 5 receptor may be followed by amino acid sequencing to identify and isolate polynucleotides which encode the kringle 5 receptor. Such polynucleotides may then be cloned into a suitable expression vector and transfected into tumor cells. Expression of the receptor by the transfected tumor cells would enhance the responsiveness of these cells to endogenous or exogenous kringle 5 peptide fragments and thereby decrease the rate of metastatic growth. Furthermore, recombinant expression of this receptor would allow greater amounts of receptor to be produced, e.g. to produce a sufficient quantity for use in high throughput screening assays to identify smaller antagonists which mimic the action of kringle 5.

Systematic substitution of amino acids within these synthesized peptides may yield high affinity peptide agonists and antagonists to the kringle 5 receptor that enhance or diminish kringle 5 peptide fragment binding to its receptor. Such agonists may be used to suppress the growth of micrometastases and thereby limit the spread of cancer. In cases of inadequate vascularization, antagonists to kringle 5 peptide fragments may be applied to block the inhibitory effects of kringle 5 peptide fragments and promote angiogenesis. For example, this type of treatment may have therapeutic effects in promoting wound healing in diabetics.

Kringle 5 peptide fragments of the present invention can also be used as antigens to generate polyclonal or monoclonal antibodies which are specific for the kringle 5 inhibitor. One way in which such antibodies could be used is in diagnostic methods and kits to detect or quantify kringle 5 peptide fragments in a body fluid or tissue. Results from these tests could be used to diagnose or determine the prognostic relevance of kringle 5 peptide fragments.

Kringle 5 peptide fragments may be labeled with radioactive isotopes (See Example 13) or chemically coupled to proteins to form conjugates. Conjugates include enzymes, carrier proteins, cytotoxic agents, fluorescent, chemiluminescent and bioluminescent molecules which are used to facilitate the testing of the ability of compounds containing kringle 5 peptide fragments to bind kringle 5 antisera, detect cell types which possess a kringle 5 peptide fragment receptor or aid in purification of kringle 5 peptide fragments. The coupling technique is generally chosen on the basis of the functional groups available on the amino acids of the kringle 5 peptide fragment sequence including, but not limited to alkyl, amino, sulfhydryl, carboxyl, amide, phenol, indolyl and imidazoyl. Various reagents used to effect such couplings include, among others, glutaraldehyde, diazotized benzidine, carbodiimides and p-benzoquinone. The efficiency of the coupling reaction is determined using different techniques appropriate for the specific reaction. For example, radiolabeling of a kringle 5 peptide or a biologically active fragment thereof with $I^{125}$ may be accomplished using chloramine T and $NaI^{125}$ of high specific activity. The reaction is terminated with sodium metabisulfite and the mixture is desalted on disposable columns. The labeled peptide is eluted from the column and the fractions are collected. Aliquots are removed from each fraction and radioactivity is measured in a gamma counter. This procedure provides the radiolabeled kringle 5 peptide fragment free from unreacted $NaI^{125}$. In another example, blood or tissue extracts containing a kringle 5 peptide fragment coupled to kringle 4 may be purified on a polylysine resin affinity column whereby the kringle 4–kringle 5 peptide fragment binds to the resin through the affinity of the kringle 4 peptide fragment for lysine. Elution of the bound protein would provide a purified kringle 4-kringle 5 peptide fragment Another application of peptide conjugation is the production of polyclonal antisera. The production of antiserum against kringle 5 peptide fragments, kringle 5 peptide fragment analogs and the kringle 5 receptor can be performed using established techniques known to those skilled in the art. For example, kringle 5 peptide fragments containing lysine residues may be linked to purified bovine serum albumin (BSA) using glutaraldehyde. The efficiency of this reaction may be determined by measuring the incorporation of radiolabeled peptide. Unreacted glutaraldehyde and peptide may be separated by dialysis, and the conjugate may be use to raise polyclonal antisera in rabbits, sheep, goats or other animals. Kringle 5 peptide fragments conjugated to a carrier molecule such as BSA may be combined with an adjuvant mixture, emulsified and injected subcutaneously at multiple sites on the back, neck, flanks, and sometimes in the footpads of a suitable host. Generally, booster injections are then given at regular intervals, such as every 2 to 4 weeks. Approximately 7 to 10 days after each injection, blood samples are obtained by venipuncture using, for example, the marginal ear veins after dilation. The blood samples are allowed to clot overnight at 4° C. and are centrifuged at approximately 2400×g at 4° C. for about 30 minutes. The serum is removed, aliquoted and stored at 4° C. for immediate use or at −20 to −90° C. for subsequent analysis.

Serum samples from generation of polyclonal antisera or media samples from production of monoclonal antisera may be analyzed for determination of antibody titer and, in particular, for the determination of high titer antisera Subsequently, the highest titer kringle 5 peptide fragment antisera may be tested to establish the following: a) optimal antiserum dilution for highest specific binding of the antigen and lowest non-specific binding, b) ability to bind increasing amounts of kringle 5 peptide fragments in a standard displacement curve, c) potential cross-reactivity with related peptides and proteins including plasminogen and kringle 5 peptide fragments of related species and d) ability to detect kringle 5 peptide fragments in cell culture media and in extracts of plasma, urine and tissues. Titer may be established through several means known in the art, such as by dot blot and density analysis and also by precipitation of radiolabeled peptide-antibody complexes using protein A, secondary antisera, cold ethanol or charcoal-dextran followed by activity measurement with a gamma counter. If desired, the highest titer antisera may be purified on affinity columns. For example, kringle 5 peptide fragments may be coupled to a commercially available resin and used to form an affinity column. Antiserum samples may then be passed through the column so that kringle 5 antibodies bind (via kringle 5 peptide fragments) to the column. These bound antibodies are subsequently eluted, collected and evaluated for determination of titer and specificity.

Kits for measurement of kringle 5 peptide fragments and the kringle 5 receptor are also contemplated as part of the present invention. Antisera that possess the highest titer and specificity and can detect kringle 5 peptide fragments in extracts of plasma, urine, tissues and cell culture media may be used to establish assay kits for rapid, reliable, sensitive and specific measurement and localization of kringle 5 peptide fragments. These assay kits may employ, but are not limited to, the following techniques: competitive and non-competitive assays, radioimmunoassays, bioluminescence and chemilumenescence assays, fluorometric assays, sandwich assays, immunoradiometric assays, dot blots, enzyme linked assays including ELISAs, microtiter plates, immunocytochemistry and antibody-coated strips or dipsticks for rapid monitoring of urine or blood. For each kit the range, sensitivity, precision, reliability, specificity and reproducibility of the assay are established by means well known to those skilled in the art.

One example of an assay kit commonly used in research and in the clinic is a radioimmunoassay (RIA) kit. A kringle 5 peptide fragment RIA may be established in the following manner: After successful radioiodination and purification of a kringle 5 peptide fragment, antiserum possessing the highest titer of anti-kringle 5 peptide fragment antibodies is added at several dilutions to tubes containing a relatively constant amount of radioactivity, such as 10,000 cpm, in a suitable buffer system. (Buffer or preimmune serum is added to other tubes to determine non-specific binding). After incubation at 4° C. for 24 hours, protein A is added to all tubes and the tubes are vortexed, incubated at room temperature for 90 minutes and centrifuged at approximately 2000–2500×g at 4° C. to precipitate the complexes of antibody bound to labeled antigen. The supernatant is removed by aspiration and radioactivity in the pellets counted in a gamma counter. The antiserum dilution that binds approximately 10 to 40% of the labeled peptide after subtraction of the non-specific binding is selected for further characterization.

Next, a dilution range (approximately 0.1 pg to 10 ng) of the kringle 5 peptide fragment used for development of the antiserum is evaluated by adding known amounts of the peptide to tubes containing radiolabeled peptide and antiserum. After an incubation period (24 or 48 hours, for example), protein A is added and the tubes are centrifuged, the supernatant is removed and the radioactivity in the pellet is counted. The displacement of the binding of radiolabeled the kringle 5 peptide fragment by the unlabeled kringle 5 peptide fragment (standard) provides a standard curve. Additionally, several concentrations of other kringle 5 peptide fragments, plasminogens, kringle 5 peptide fragments from different species and homologous peptides may be added to the assay tubes to characterize the specificity of the kringle 5 peptide fragment antiserum.

Thereafter, extracts of various tissues including, but not limited to, primary and secondary tumors, Lewis lung carcinoma, cultures of kringle 5 peptide fragment-producing cells, placenta, uterus and other tissues such as brain, liver and intestine are prepared using extraction techniques that have been successfully employed to extract kringle 5 peptide fragments. After workup of the tisssue extracts, assay buffer is added and different aliquots are placed into the RIA tubes. Extracts of known kringle 5 peptide fragment-producing cells produce displacement curves that are parallel to the standard curve whereas extracts of tissues that do not produce kringle 5 peptide fragments do not displace radiolabeled kringle 5 peptide fragments from the kringle 5 peptide fragment antiserum. Such displacement curves indicate the utility of the kringle 5 peptide fragment assay to measure kringle 5 peptide fragments in tissues and body fluids.

Tissue extracts that contain kringle 5 peptide fragments may also be characterized by subjecting aliquots to reverse phase HPLC. Eluate fractions are collected, dried in Speed Vac, reconstituted in RIA buffer and analyzed in the kringle 5 RIA. In this case, the maximal amount of kringle 5 peptide fragment immunoreactivity is located in the fractions corresponding to the elution position of the kringle 5 peptide fragment.

The above described assay kit would provide instructions, antiserum, a kringle 5 peptide fragment and possibly a radiolabeled kringle 5 peptide fragment and/or reagents for precipitation of bound kringle 5 peptide fragment/kringle 5 antibody complexes. Such a kit would be useful for the measurement of kringle 5 peptide fragments in biological fluids and tissue extracts of animals and humans with and without tumors.

Another kit may be used to visualize or localize kringle 5 peptide fragments in tissues and cells. For example, immunohistochemistry techniques and kits which employ such techniques are well known to those of ordinary skill in the art. As is known in the art, an immunohistochemistry kit would provide kringle 5 peptide fragment antiserum; and possibly blocking serum and secondary antiserum linked to a fluorescent molecule such as fluorescein isothiocyanate or to some other reagent used to visualize the primary antiserum. Using this methodology, biopsied tumors may be examined for sites of kringle 5 peptide fragment production or for sites of the kringle 5 peptide fragment receptor. Alternatively, a kit may supply radiolabeled nucleic acids for use in in situ hybridization to probe for kringle 5 peptide fragment messenger RNA.

The compounds of the invention may be prepared using processes well known to those of ordinary skill in the art. (See for example, Sottrup-Jensen et al., Progress in Chemical Fibrinolysis and Thrombolysis, Vol. 3, Davidson, J. F., Rowan, R. M., Samama, M. M. and Desnoyers, P. C. editors, Raven Press, New York, 1978. One manner of preparing kringle 5 peptide fragments is by enzymatic cleavage of the native protein (glu-plasminogen) or a variant thereof (meaning a truncated form of the full length protein which is amenable to cleavage by enzymatic digestion and which comprises at least a kringle 5 sequence as defined above such as lys-plasminogen or miniplasminogen). This method first requires isolating the protein from human plasma in the absence of plasmin inhibitors and thereby promoting the conversion of glu-plasminogen to lys-plasminogen (see Novokhatny, V and Kudinov, S. A., J. Mol. Biol. 179: 215–232 (1984). Subsequently, the truncated molecule is treated with an proteolytic enzyme at a concentration sufficient to cleave kringle 5 peptide fragments from the polypeptide and then purified from the remaining fragments by means known to those skilled in the art. A preferred proteolytic enzyme is human or porcine elastase which cleaves plasminogen and its truncated variants between kringle regions 3–4 and 4–5 (and is thereby capable of forming peptide fragments containing kringles 1–3 and 1–4 or kringles 4 or 5 alone). For example, lys-plasminogen or glu-plasminogen may be treated with porcine or human neutrophyl elastase at a ratio of about 1:100–1:300 lys-plasminogen:elastase (preferably at a ratio of 1:150–1:250 and most preferably at a ratio of 1:150 in a buffer solution (such as Tris-HCl, NaCl, sodium phosphate and the like). Alternatively, the elastase may first be immobilized (such as to a resin) to facilitate purification of the cleavage products. The glu-plasminogen or lys-plaminogen is generally treated with human or porcine elastase at temperatures ranging from about 10° C. to about 40° C. and for time periods ranging from about 4 to about 24 hours depending on the extent of cleavage desired. To achieve complete digestion of glu-plasminogen, lys-plasminogen or miniplasminogen with human or porcine elastase requires exposure of these polypeptides to the enzyme for at least about 12 hours at room temperature. Varying the pH and exposure time to the enzyme results in less or partial cleavage at one or more of the susceptible cleavage sites. The cleavage products are then purified by any means well known in the art (such as column chromatography). A preferred purification scheme involves applying the cleavage products to a lysine-Sepharose column as described in Example 14.

Solid Phase Synthesis of Kringle 5 Peptide Fragments

The following examples will serve to further illustrate the preparation of the novel compounds of the invention:

EXAMPLE 1

N-Ac-Val-Leu-Leu-Pro-Asp-Val-Glu-Thr-Pro-Ser-Glu-Glu-Asp-NH$_2$

An amide peptide synthesis column (Applied Biosystems) was placed in the peptide synthesis column position of a Perkin Elmer/Applied Biosynthesis "Synergy" peptide synthesizer, and the following synthetic sequence was used:
1. Solvating the resin with DMF for about 5 minutes;
2. Deblocking the Fmoc group from the α-N-terminal of the resin-bound amino acid using 20% piperidine in DMF for about 15 minutes;
3. Washing the resin with DMF for about 5 minutes;
4. Activating the α-C-terminal of amino acid No. 1 (Fmoc-Asp(β-O$^t$Bu), 25 μmol) using a 0.2 M solution of HBTU (25 μmol) and HOBT (25 μmol) in DMSO-NMP (N-methylpyrrolidone) and a 0.4 M solution of diisopropylethylamine (25 μmol) in DMSO-NMP and coupling the activated amino acid to the resin;
5. Coupling the activated Fmoc-protected amino acid (prepared in step 5) to the resin-bound amino acid (prepared in step 2) in DMF for about 30 minutes;
6. Washing with DMF for 5 minutes;
7. Repeating steps 3 through 6 with the following amino acids:

| No. | Amino Acid |
| --- | --- |
| 2. | Fmoc-Glu(γ-O$^t$Bu) |
| 3. | Fmoc-Glu(γ-O$^t$Bu) |
| 4. | Fmoc-Ser($^t$Bu) |
| 5. | Fmoc-Pro |
| 6. | Fmoc-Thr($^t$Bu) |
| 7. | Fmoc-Glu(γ-O$^t$Bu) |
| 8. | Fmoc-Val |
| 9. | Fmoc-Asp(β-O$^t$Bu) |
| 10. | Fmoc-Pro |
| 11. | Fmoc-Leu |
| 12. | Fmoc-Leu |
| 13. | Fmoc-Val |

8. Coupling acetic acid to the α-N-terminal of the resin-bound peptide via the conditions of steps 4 and 5.
9. Washing the resin with THF for about 5 minutes to remove DMF and shrink the resin, then drying the resin with argon for 10 minutes and nitrogen for 10 minutes more to provide clean, resin-bound peptide.
10. Cleaving of the peptide from the resin with concomitant deprotection of amino acid side chains by stirring with cleavage reagent (freshly-prepared thioanisole (100 μL), water (50 μL), ethanedithiol (50 μL) and trifluoroacetic acid (1.8 mL) mixed in the above order at −5° C. to −10° C.) at 0° C. for 10–15 minutes and then at ambient temperature for an additional 1.75 hours (plus an additional 0.5 hour for each Arg(Pmc), if present). The amount of cleavage reagent used was determined by the following formula:

| weight of resin with bound peptide (mg) | amount of cleavage reagent (μL) |
| --- | --- |
| 0–10 | 100 |
| 10–25 | 200 |
| 25–50 | 400 |
| 50–100 | 700 |
| 100–200 | 1200 |

11. Filtering and rinsing the produdct with neat trifluoroacetic acid, adding the filtrate in 0.5 mL portions to a centrifuge tube containing about 8 mL of cold diethyl ether, centrifuging and decanting and repeating the process until all of the peptide precipitated (if the peptide did not precipitate upon addition to ether, the mixture was extracted with aqueous 30% aqueous acetic acid (3×1 mL), and the combined aqueous extracts were lyophilized to provide the product).
12. Using the peptide crude or purifying the peptide by HPLC using a 7 μm Symmetry Prep C18 column (7.8× 300 mm) with solvent mixtures varying in a gradient from 5% to 100% acetonitrile-(water, 0.1% TFA) over a period of 50 minutes followed by lyophilizing to provide 35 mg of N-Ac-Val-Leu-Leu-Pro-Asp-Val-Glu-Thr-Pro-Ser-Glu-Glu-Asp-NH$_2$.

EXAMPLE 2

N-Ac-Met-Phe-Gly-Asn-Gly-Lys-Gly-Tyr-Arg-Gly-Lys-Arg-Ala-Thr-Thr-Val-Thr-Gly-Thr-Pro-NH$_2$

The title compound was prepared using the synthetic sequence described in Example 1 and using Fmoc-Pro as amino acid No. 1. The following amino acids were added using the conditions indicated:

| No. | Amino Acid |
| --- | --- |
| 2. | Fmoc-Thr($^t$Bu) |
| 3. | Fmoc-Gly |
| 4. | Fmoc-Thr($^t$Bu) |
| 5. | Fmoc-Val |
| 6. | Fmoc-Thr($^t$Bu) |
| 7. | Fmoc-Thr($^t$Bu) |
| 8. | Fmoc-Ala |
| 9. | Fmoc-Arg(Pmc) |
| 10. | Fmoc-Lys(Boc) |
| 11. | Fmoc-Gly |
| 12. | Fmoc-Arg(Pmc) |
| 13. | Fmoc-Tyr($^t$Bu) |
| 14. | Fmoc-Gly |
| 15. | Fmoc-Lys(Boc) |
| 16. | Fmoc-Gly |
| 17. | Fmoc-Asn(Trt) |
| 18. | Fmoc-Gly |
| 19. | Fmoc-Phe |
| 20. | Fmoc-Met | to provide 35 mg of N-Ac-Met-Phe-Gly-Asn-Gly-Lys-Gly-Tyr-Arg-Gly-Lys-Arg-Ala-Thr-Thr-Val-Thr-Gly-Thr-Pro-NH$_2$.

EXAMPLE 3

Ac-Gln-Asp-Trp-Ala-Ala-Gln-Glu-Pro-His-Arg-His-Ser-Ile-Phe-Thr-Pro-Glu-Thr-Asn-Pro-Arg-Ala-Gly-Leu-Glu-Lys-Asn-Tyr-NH$_2$

The title compound was prepared using the synthetic sequence described in Example 1 and using Fmoc-Tyr($^t$Bu)

as amino acid No. 1. The following amino acids were added using the conditions indicated:

| No. | Amino Acid |
|---|---|
| 2. | Fmoc-Asn(Trt) |
| 3. | Fmoc-Lys(Boc) |
| 4. | Fmoc-Glu(γ-O$^t$Bu) |
| 5. | Fmoc-Leu |
| 6. | Fmoc-Gly |
| 7. | Fmoc-Ala |
| 8. | Fmoc-Arg(Pmc) |
| 9. | Fmoc-Pro |
| 10. | Fmoc-Asn(Trt) |
| 11. | Fmoc-Thr($^t$Bu) |
| 12. | Fmoc-Glu(γ-O$^t$Bu) |
| 13. | Fmoc-Pro |
| 14. | Fmoc-Thr($^t$Bu) |
| 15. | Fmoc-Phe |
| 16. | Fmoc-Ile |
| 17. | Fmoc-Ser($^t$Bu) |
| 18. | Fmoc-His(Trt) |
| 19. | Fmoc-Arg(Pmc) |
| 20. | Fmoc-His(Trt) |
| 21. | Fmoc-Pro |
| 22. | Fmoc-Glu(γ-O$^t$Bu) |
| 23. | Fmoc-Gln(Trt) |
| 24. | Fmoc-Ala |
| 25. | Fmoc-Ala |
| 26. | Fmoc-Trp |
| 27. | Fmoc-Asp(β-O$^t$Bu) |
| 28. | Fmoc-Gln(Trt) | to provide 40 mg of N-Ac-Gln-Asp-Trp-Ala-Ala-Gln-Glu-Pro-His-Arg-His-Ser-Ile-Phe-Thr-Pro-Glu-Thr-Asn-Pro-Arg-Ala-Gly-Leu-Glu-Lys-Asn-Tyr-NH$_2$.

EXAMPLE 4

N-Ac-Arg-Asn-Pro-Asp-Gly-Asp-Val-Gly-Gly-Pro-Trp-NH$_2$

The title compound was prepared using the synthetic sequence described in Example 1 and using Fmoc-Trp as amino acid No. 1. The following amino acids were added using the conditions indicated:

| No. | Amino Acid |
|---|---|
| 2. | Fmoc-Pro |
| 3. | Fmoc-Gly |
| 4. | Fmoc-Gly |
| 5. | Fmoc-Val |
| 6. | Fmoc-Asp(β-O$^t$-Bu) |
| 7. | Fmoc-Gly |
| 8. | Fmoc-Asp(β-O$^t$-Bu) |
| 9. | Fmoc-Pro |
| 10. | Fmoc-Asn(Trt) |
| 11. | Fmoc-Arg(Pmt) | to provide 20 mg of N-Ac-Arg-Asn-Pro-Asp-Gly-Asp-Val-Gly-Gly-Pro-Trp-NH$_2$.

EXAMPLE 5

N-Ac-Tyr-Thr-Thr-Asn-Pro-Arg-Lys-Leu-Tyr-Asp-Tyr-NH$_2$

The title compound was prepared using the synthetic sequence described in example 1 and using Fmoc-Tyr($^t$Bu) as amino acid No. 1. The following amino acids were added using the conditions indicated:

| No. | Amino Acid |
|---|---|
| 2. | Fmoc-Asp(β- O$^t$Bu) |
| 3. | Fmoc-Tyr($^t$Bu) |
| 4. | Fmoc-Leu |
| 5. | Fmoc-Lys(Boc) |
| 6. | Fmoc-Arg(Pmc) |
| 7. | Fmoc-Pro |
| 8. | Fmoc-Asn(Trt) |
| 9. | Fmoc-Thr($^t$Bu) |
| 10. | Fmoc-Thr($^t$Bu) |
| 11. | Fmoc-Tyr($^t$Bu) | to provide 10 mg of N-Ac-Tyr-Thr-Thr-Asn-Pro-Arg-Lys-Leu-Tyr-Asp-Tyr-NH$_2$.

EXAMPLE 6

N-Ac-Pro-Arg-Lys-Leu-Tyr-Asp-Tyr-NH$_2$

The title compound was prepared using the synthetic sequence described in Example 1 and using Fmoc-Tyr($^t$Bu) as amino acid No. 1. The following amino acids were added using the conditions indicated:

| No. | Amino Acid |
|---|---|
| 2. | Fmoc-Asp(β-O$^t$Bu) |
| 3. | Fmoc-Tyr($^t$Bu) |
| 4. | Fmoc-Leu |
| 5. | Fmoc-Lys(Boc) |
| 6. | Fmoc-Arg(Pmc) |
| 7. | Fmoc-Pro | to provide N-Ac-Pro-Arg-Lys-Leu-Tyr-Asp-Tyr-NH$_2$ (4 mg). MS (FAB) m/z 995 (M+H)$^+$.

EXAMPLE 7

N-Ac-Pro-Arg-Lys-Leu-Tyr-Asp-NH$_2$

The title compound was prepared using the synthetic sequence described in Example 1. The following amino acids were added using the conditions indicated:

| No. | Amino Acid |
|---|---|
| 2. | Fmoc-Tyr($^t$Bu) |
| 3. | Fmoc-Leu |
| 4. | Fmoc-Lys(Boc) |
| 5. | Fmoc-Arg(Pmc) |
| 6. | Fmoc-Leu | to provide N-Ac-Pro-Arg-Lys-Leu-Tyr-Asp-NH$_2$ (6 mg). MS (ESI) m/z 832 (M+H)$^+$.

EXAMPLE 8

N-Ac-Pro-Glu-Lys-Arg-Tyr-Asp-Tyr-NH$_2$

The title compound was prepared using the synthetic sequence described in Example 1 and using Fmoc-Tyr($^t$Bu) as amino acid No. 1. The following amino acids were added using the conditions indicated:

| No. | Amino Acid |
|---|---|
| 2. | Fmoc-Asp(β-O$^t$Bu) |
| 3. | Fmoc-Tyr($^t$Bu) |
| 4. | Fmoc-Arg(Pmc) |
| 5. | Fmoc-Lys(Boc) |
| 6. | Fmoc-Glu |
| 7. | Fmoc-Pro | to provide N-Ac-Pro-Glu-Lys-Arg-Tyr-Asp-Tyr-NH$_2$ (6 mg). MS (FAB) m/z (1101) (M+H)$^+$.

EXAMPLE 9

N-Ac-Arg-Lys-Leu-Tyr-Asp-Tyr-NH$_2$

The title compound was prepared using the synthetic sequence described in Example 1 and using Fmoc-Tyr($^t$Bu) as amino acid No. 1. The following amino acids were added using the conditions indicated:

| No. | Amino Acid |
|---|---|
| 2. | Fmoc-Asp(β-O$^t$Bu) |
| 3. | Fmoc-Tyr($^t$Bu) |
| 4. | Fmoc-Leu |
| 5. | Fmoc-Lys(Boc) |
| 6. | Fmoc-Arg(Pmc) | to provide N-Ac-Arg-Lys-Leu-Tyr-Asp-Tyr-NH$_2$ (8 mg). MS (ESI) m/z 898 (M+H)$^+$.

EXAMPLE 10

N-Ac-Pro-Arg-Lys-Leu-3-I-Tyr-Asp-Tyr-NH$_2$ (SEQ ID NO: 13)

The title compound was prepared using the synthetic sequence described in Example 1 and using Fmoc-Tyr($^t$Bu) as amino acid No. 1. The following amino acids were added using the conditions indicated:

| No. | Amino Acid |
|---|---|
| 2. | Fmoc-Asp(β-O$^t$Bu) |
| 3. | Fmoc-3-I-Tyr($^t$Bu) |
| 4. | Fmoc-Leu |
| 5. | Fmoc-Lys(Boc) |
| 6. | Fmoc-Arg(Pmc) |
| 7. | Fmoc-Pro | to provide N-Ac-Pro-Arg-Lys-Leu-3-I-Tyr-Asp-Tyr-NH$_2$ (2 mg). MS (ESI) m/z (1121) (M+H)$^+$.

EXAMPLE 11

N-Ac-Pro-Arg-Lys-Leu-Tyr-Asp-3-I-Tyr-NH$_2$ (SEQ ID NO: 14)

The title compound was prepared using the synthetic sequence described in Example 1 and using Fmoc-3-I-Tyr ($^t$Bu) as amino acid No. 1. The following amino acids were added using the conditions indicated:

| No. | Amino Acid |
|---|---|
| 2. | Fmoc-Asp(β-O$^t$Bu) |
| 3. | Fmoc-Tyr($^t$Bu) |
| 4. | Fmoc-Leu |
| 5. | Fmoc-Lys(Boc) |
| 6. | Fmoc-Arg(Pmc) |
| 7. | Fmoc-Pro | to provide N-Ac-Pro-Arg-Lys-Leu-Tyr-Asp-3-I-Tyr-NH$_2$ (2.5 mg). MS (ESI) m/z 1121 (M+H)$^+$.

EXAMPLE 12

N-Ac-Lys-Leu-Tyr-Asp-NH$_2$

The title compound was prepared using the synthetic sequence described in Example 1 and using Fmoc-Asp(β-O$^t$Bu) as amino acid No. 1. The following amino acids were added using the conditions indicated:

| No. | Amino Acid |
|---|---|
| 2. | Fmoc-Tyr($^t$Bu) |
| 3. | Fmoc-Leu |
| 4. | Fmoc-Lys | to provide 2 mg of N-Ac-Lys-Leu-Tyr-Asp-NH$_2$ (2 mg).

EXAMPLE 13

Preparation and separation of a mixture N-Ac-Pro-Arg-Lys-Leu-Tyr-Asp-3-I$^{125}$-Tyr$^{535}$-NH$_2$ and N-Ac-Pro-Arg-Lys-Leu-3-I$^{125}$-Tyr$^{533}$-Asp-Tyr-NH$_2$ (SEQ ID NO: 13) and (SEQ NO: ID 14), Respectively To a solution of 30 μg of N-acetyl-prolyl-arginyl-lysyl-leucyl-tyrosyl-aspartyl-tyrosylamide in 80 mL of phosphate buffered saline (PBS) was added one iodobead (Pierce, Rockford, Ill.) and 100 μCi of NaI$^{125}$. After 10 minutes, the excess NaI$^{125}$ reagent was removed by applying the reaction mixture to a Waters C18-Light SepPack column and eluting with water then 0.1% TFA in 1:1 CH$_3$CN/water and collecting 3×200 μL fractions to provide a mixture of Tyr$^{533}$- and Tyr$^{535}$- radiolabeled peptides.

The hot peptide mixture was coinjected onto a C18 HPLC column with an equimolar solution of cold carriers N-Ac-Pro-Arg-Lys-Leu-Tyr-Asp-3-I-Tyr-NH$_2$ and N-Ac-Pro-Arg-Lys-Leu-3-I-Tyr-Asp-Tyr-NH$_2$, the elution times of which had been predetermined as 36 and 38 minutes, respectively. Repeated elutions with the solvent system in Example 1 and lyophylization of the combined, relevant fractions provided the desired compound N-Ac-Pro-Arg-Lys-Leu-Tyr-Asp-3-I-Tyr-NH$_2$ with a minimal impurity N-Ac-Pro-Arg-Lys-Leu-3-I-Tyr-Asp-Tyr-NH$_2$.

General Methodologies

EXAMPLE 14

Isolation and Purification of Kringle 5 Peptide Fragments

The kringle 5 peptide fragments were prepared from the digestion of Lys plasminogen (Lys-HPg, Abbott Laboratories, Abbott Park, Ill.) with porcine elastase (SIGMA, St. Louis, Mo.) by a modification of the method of Powell et al. (Arch Biochem. Biophys. 248 (1): 390–400 (1986), which is hereby incorporated herein by reference).

1.5 mg of porcine elastase was incubated with 200 mg of Lys-HPg in 50 mM Tris-HCl pH 8.0 and rocked overnight at room temperature. The reaction was terminated by the addition of DPF (diisopropyl fluorophosphate, SIGMA) to a final concentration of 1 mM. The mixture was rocked for an additional 30 minutes, dialysed against 50 mM Tris pH 8.0 overnight and concentrated. The cleaved plasminogen was placed over a 2.5 cm×15 cm lysine-Sepharose 4B column (Brockway, W. J. and Castellino, F. J., *Arch. Biochem. Biophys.* 151: 194–199 (1972), which is hereby incorporated by reference) and equilibrated with 50 mM Tris pH 8.0 until an absorbance of 0.05 (at 280 nm) was reached. (This step was performed to remove any fragments containing a kringle 1 region and/or a kringle 4 region (both of which bind lysine)). The non-absorbed kringle 5 peptide fragments were dialysed against 50 mM $Na_2PO_4$ buffer, pH 5.0 then applied to a BioRad Mono-S column equilibrated with the same buffer. The cleaved kringle 5 portion, uncut mini-HPg and remaining protease domain fraction were eluted with a 0–20%, 20–50% and 50–70% step gradient of 20 mM Phosphate/1 M KCl pH 5.0. The kringle 5 peptide fragments eluted at the 50% step as determined by gel electrophesis. The collected peak was dialysed overnight against 20 mM Tris pH 8.0.

The separated kringle 5 fragments were determined to be at least 95% pure by FPLC chromatography and DodSO4/PAGE with silver staining (Coomasie Blue). Sequence analysis of the amino terminal portion of the purified fragments revealed the presence of three polypeptides having α-N-terminus sequences of VLLPDVETPS, VAPPPVVLL and VETPSEED whch correspond to amino acid positions $Val^{449}$-$Ser^{458}$, $Val^{443}$-$Leu^{450}$ and $Val^{454}$-$Asp^{461}$ of SEQ ID. NO: 1, respectively.

EXAMPLE 15

Endothelial Proliferation Assay

The in vitro proliferation of endothelial cells was determined as described by Lingen, et al., in *Laboratory Investigation*, 74: 476–483 (1996), which is hereby incorporated herein by reference, using the Cell Titer 96 Aqueous Non-Radioactive Cell Proliferation Assay kit (Promega Corporation, Madison, Wis.). Bovine capillary (adrenal) endothelial cells were plated at a density of 1000 cells per well in a 96-well plate in Dulbecco's Modified Eagle Medium (DMEM) containing 10% donor calf serum and 1% BSA (bovine serum albumin, GIBCO BRL, Gaithersburg, Md.). After 8 hours, the cells were starved overnight in DMEM containing 0.1% BSA then re-fed with media containing specified concentrations of inhibitor and 5 ng/mL bFGF (basic fibroblast growth factor). The results of the assay were corrected both for unstimulated cells (i.e. no bFGF added) as the baseline and for cells stimulated with bFGF alone (i.e. no inhibitor added) as the maximal proliferation. When multple experiments were combined, the results were represented as the percent change in cell number as compared to bFGF alone.

EXAMPLE 16

Endothelial Cell Migration Assay

The endothelial cell migration assay was performed essentially as described by Polverini, P. J. et al., *Methods Enzymol*, 198: 440–450 (1991), which is hereby incorporated herein by reference. Briefly, bovine capillary (adrenal) endothelial cells (BCE, supplied by Judah Folkman, Harvard University Medical School) were starved overnight in DMEM containing 0.1% bovine serum albumin (BSA). Cells were then harvested with trypsin and resuspended in DMEM with 0.1% BSA at a concentration of $1.5 \times 10^6$ cells/mL. Cells were added to the bottom of a 48-well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.1% gelatin overnight and dried. The chamber was then reinverted and test substances were added to the wells of the upper chamber (to a total volume of 50 μL); the apparatus was then incubated for 4 hours at 37° C. Membranes were recovered, fixed and stained (DiffQuick, Fisher Scientific, Pittsburgh, Pa.) and the number of cells that had migrated to the upper chamber per 10 high power fields were counted. Background migration to DMEM+0.1% BSA was subtracted and the data reported as the number of cells migrated per 10 high power fields (400X) or when results from multiple experiments were combined, as the percent inhibition of migration compared to a positive control. The results are shown in Table 1.

EXAMPLE 17

Effect of Kringle 5 Peptide Fragments on Endothetial Cell Proliferation in vitro The effect of kringle 5 peptide fragments on endothelial cell proliferation was determined in vitro using the above described endothelial cell proliferation assay. For these experiments, kringle 5 peptide fragments was prepared as illustrated in Examples 1 through 14 and tested at various concentrations ranging from about 100 to 1000 pM with bFGF used as a maximum proliferation control. The kringle 5 peptide fragment SEQ ID NO: 3 was effective at inhibiting BCE cell proliferation in a dose-dependent manner. The concentration of kringle 5 peptide fragment SEQ ID NO: 3 required to reach 50% inhibition ($ED_{50}$) was determined at about 300 pM. In contrast, the $ED_{50}$ of kringles 1–4 was shown to be 135 nM.

A summary of the effect of other kringle peptide fragments on inhibition of BCE cell proliferation is shown in Table 1. The kringle 3 peptide fragment was least effective at inhibitng BCE cell proliferation ($ED_{50}$=460 nM), followed by the kringle 1 peptide fragment ($ED_{50}$=320 nM), kringle 1–4 peptide fragments ($ED_{50}$=135 nM) and kringles 1–3 peptide fragments ($ED_{50}$=75 nM). The kringle 5 peptide fragment was the most effective at inhibiting BCE cell proliferation with an $ED_{50}$ of 0.3 nM.

EXAMPLE 18

Effect of Kringle 5 Peptide Fragments on Endothelial Cell Migration in vito

The effect of kringle 5 peptide fragments on endothelial cell migration was also determined in vitro using the above described endothelial cell migration assay. Kringle 5 peptide fragments inhibited BCE cell migration in a dose-dependent fashion with an $ED_{50}$ of approximately 300 pM. At the concentration of kringle 5 peptide fragments required for maximal inhibition of BCE cells, PC-3 cells and MDA 486 cells were also inhibited. This result, taken together with the result in Example 2, indicates that the inhibition of stimulated proliferation and migration of BCE cells by kringle 5 peptide fragments is both potent and specific to endothelial cells and not to normal or tumor cells.

The foregoing are merely illustrative of the invention and are not intended to limit the invention to the disclosed compounds. Variations and changes which are obvious to one skilled in the art are intended to be within the scope and nature of the invention which are defined in the appended claims.

Table 1 shows a summary of $ED_{50}$ values obtained from the inhibition of various kringle fragments on BCE cell proliferation and cell migration in vitro. In the table, kringle peptide fragments are labeled according to their corresponding sequence homology to SEQ ID NO: 1. The symbol "*" indicates data taken from Marti, D., et al., Eur. J. Biochem., 219: 455–462 (1994), which is hereby incorporated by reference.

TABLE 1

| Protein Fragment from SEQ ID NO:1 | Antiproliferative Activity of BCE Cells ($ED_{50}$) | Migratory Inhibition of HMVEC Cells ($ED_{50}$) |
|---|---|---|
| kringles 1–4(angiostatin)* | 135 nM | 160 nM |
| kringle 1 (Tyr$^{80}$-Glu$^{163}$)* | 320 nM | — |
| kringle 2 (Glu$^{161}$-Thr$^{245}$)* | no activity | — |
| kringle 3 (Thr$^{253}$-Ser$^{335}$)* | 460 nM | — |
| kringle 4 (Val$^{354}$-Val$^{443}$)* | no activity | — |
| kringles 1–3 (Tyr$^{80}$-Pro$^{353}$)* | 75 nM | 60 nM |
| kringles 2–3 (Glu$^{161}$-Ser$^{335}$)* | — | — |
| kringle 5 (Val$^{443}$-Ala$^{543}$) | 250 pM | 200 pM |
| kringle 5 (Val$^{449}$-Ala$^{543}$) | — | 240 pM |
| kringle 5 (Val$^{454}$-Ala$^{543}$) | — | 220 pM |
| kringle 5 (Val$^{443}$-Phe$^{546}$) | 60 nM | 55 nM |
| kringle 5 (Val$^{449}$-Phe$^{546}$) | — | — |
| kringle 5 (Val$^{454}$-Phe$^{546}$) | — | — |
| kringles 4–5 (Val$^{355}$-Ala$^{543}$) | — | 280 pM |

TABLE 1-continued

| Protein Fragment from SEQ ID NO:1 | Antiproliferative Activity of BCE Cells ($ED_{50}$) | Migratory Inhibition of HMVEC Cells ($ED_{50}$) |
|---|---|---|
| kringles 4–5 (Val$^{355}$-Phe$^{546}$) | — | — |
| N-Ac-Val$^{449}$-Asp$^{461}$-NH$_2$ | — | >1 mM |
| N-Ac-Met$^{463}$-Pro$^{482}$-NH$_2$ | — | >1 mM |
| N-Ac-Gln$^{484}$-Tyr$^{511}$-NH$_2$ | — | >100 μM |
| N-Ac-Arg$^{513}$-Trp$^{523}$-NH$_2$ | — | 500 pM |
| N-Ac-Tyr$^{525}$-Trp$^{535}$-NH$_2$ | — | 200 pM |
| N-Ac-Pro$^{529}$-Tyr$^{535}$-NH$_2$ | — | 120 pM |
| N-Ac-Pro$^{529}$-Asp$^{534}$-NH$_2$ | — | 123 pM |
| N-Ac-Pro$^{150}$-Tyr$^{156}$-NH$_2$ | — | 160 nM |
| N-Ac-Arg$^{530}$-Tyr$^{535}$-NH$_2$ | — | 80 nM |
| N-Ac-Pro-Arg-Lys-Leu-3-I-Tyr-Asp-Tyr-NH$_2$ | — | >100 nM |
| N-Ac-Pro-Arg-Lys-Leu-Tyr-Asp-3-I-Tyr-NH$_2$ | — | 400 pM |
| N-Ac-Lys$^{531}$-Tyr$^{534}$-NH$_2$ | — | — |

What is claimed is:

1. A method of treating a disease in a patient in need of antiangiogenesis therapy comprising adminstering to a human or animal a therapeutically effective amount of a mammalian kringle 5 peptide fragment.

2. The method of claim 1 wherein said mammalian kringle 5 peptide fragment is selected from the group consisting of human, murine, bovine, Rhesus monkey and porcine kringle 5 peptide fragment.

3. The method of claim 2 wherein said kringle 5 peptide fragment is a human kringle 5 peptide fragment.

4. The method of claim 1 wherein said disease is selected from the group consisting of cancer, arthritis, macular degeneration and diabetic retinopathy.

5. The method of claim 4 wherein said disease is cancer.

6. The method of claim 5 wherein said disease is selected from primary and metastatic solid tumors, carcinomas, sarcomas, lymphomas, psoriasis and hemagiomas.

7. A method of inhibiting endothelial cell proliferation, comprising administering to an endothelial cell an effective amount of a protein having an amino acid sequence encoding a kringle 5 peptide fragment of a plasminogen molecule.

8. The method of claim 7, wherein said plasminogen molecule is human plasminogen.

9. The method of claim 7, wherein said protein is selected from the group consisting of SEQ ID NO: 2, SEQ ID NO: 3, SEQ ID NO: 4, SEQ ID NO: 5, SEQ ID NO: 6, SEQ ID NO: 7.

10. A method of treating a disease in a patient in need of antiangiogenesis therapy comprising administering to a human or animal a therapeutically effective amount of a compound of the formula $$A\text{-}B\text{-}C\text{-}X\text{-}Y \qquad (I),$$

or a pharmaceutically acceptable salt, ester or prodrug thereof, wherein

A is absent or a nitrogen protecting group;

Y is absent or a carboxylic acid protecting group;

B is absent or is from 1 to about 197 naturally-occurring amino acid residues having substantial sequence homology to the corresponding amino acid sequence from about amino acid position 334 to amino acid position 530 of SEQ ID NO: 1;

C is $R^1$-$R^2$-$R^3$-$R^4$ wherein $R^1$ is lysyl, $R^2$ is leucyl or arginyl, $R^3$ is tyrosyl, 3-I-tyrosyl or phenylalanyl; and $R^4$ is aspartyl, and X is absent or is from 1 to about 12 naturally occurring amino acid residues having substantial sequence homology to the corresponding amino acid sequence from amino acid position 535 to about amino acid position 546 of SEQ ID NO: 1.

11. The method of claim 10 wherein B is present and A, C, X, and Y are as defined therein.

12. The method of claim 10 wherein A and Y are absent and B, C, and X are as defined therein.

* * * * *

UNITED STATES PATENT AND TRADEMARK OFFICE
CERTIFICATE OF CORRECTION

PATENT NO. : 5,981,484
DATED : November 9, 1999
INVENTOR(S) : Donald J. Davidson It is certified that error appears in the above-identified patent and that said Letters Patent is hereby corrected as shown below:

Col. 1, line 17
      replace "angiostatin"
      with --kringle 5--.
    Col. 1, line 18
      replace "angiostatin"
      with --kringle 5--.
    Col. 1, line 19
      replace "angiostatin"
      with --kringle 5--.

Signed and Sealed this

First Day of May, 2001

Attest:

NICHOLAS P. GODICI

Attesting Officer        Acting Director of the United States Patent and Trademark Office

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 791 amino acids
      (B) TYPE: amino acid
      (D) TOPOLOGY: linear (ii) MOLECULE TYPE:
      (A) DESCRIPTION: protein (xi) SEQUENCE DESCRIPTION: SEQ ID NO:1:

```
Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
                20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
        50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
               100                 105                 110

Pro His Arg Pro Arg Phe Ser Pro Ala Thr His Pro Ser Glu Gly Leu
           115                 120                 125

Glu Glu Asn Tyr Cys Arg Asn Pro Asp Asn Asp Pro Gln Gly Pro Trp
```

```
            130                 135                 140
Cys Tyr Thr Thr Asp Pro Glu Lys Arg Tyr Asp Tyr Cys Asp Ile Leu
145                 150                 155                 160
Glu Cys Glu Glu Glu Cys Met His Cys Ser Gly Glu Asn Tyr Asp Gly
                    165                 170                 175
Lys Ile Ser Lys Thr Met Ser Gly Leu Glu Cys Gln Ala Trp Asp Ser
                180                 185                 190
Gln Ser Pro His Ala His Gly Tyr Ile Pro Ser Lys Phe Pro Asn Lys
            195                 200                 205
Asn Leu Lys Lys Asn Tyr Cys Arg Asn Pro Asp Arg Glu Leu Arg Pro
            210                 215                 220
Trp Cys Phe Thr Thr Asp Pro Asn Lys Arg Trp Glu Leu Cys Asp Ile
225                 230                 235                 240
Pro Arg Cys Thr Thr Pro Pro Ser Ser Gly Pro Thr Tyr Gln Cys
                    245                 250                 255
Leu Lys Gly Thr Gly Glu Asn Tyr Arg Gly Asn Val Ala Val Thr Val
                260                 265                 270
Ser Gly His Thr Cys Gln His Trp Ser Ala Gln Thr Pro His Thr His
            275                 280                 285
Asn Arg Thr Pro Glu Asn Phe Pro Cys Lys Asn Leu Asp Glu Asn Tyr
            290                 295                 300
Cys Arg Asn Pro Asp Gly Lys Arg Ala Pro Trp Cys His Thr Thr Asn
305                 310                 315                 320
Ser Gln Val Arg Trp Glu Tyr Cys Lys Ile Pro Ser Cys Asp Ser Ser
                    325                 330                 335
Pro Val Ser Thr Glu Gln Leu Ala Pro Thr Ala Pro Glu Leu Thr
                340                 345                 350
Pro Val Val Gln Asp Cys Tyr His Gly Asp Gly Gln Ser Tyr Arg Gly
                    355                 360                 365
Thr Ser Ser Thr Thr Thr Thr Gly Lys Lys Cys Gln Ser Trp Ser Ser
            370                 375                 380
Met Thr Pro His Arg His Gln Lys Thr Pro Glu Asn Tyr Pro Asn Ala
385                 390                 395                 400
Gly Leu Thr Met Asn Tyr Cys Arg Asn Pro Asp Ala Asp Lys Gly Pro
                    405                 410                 415
Trp Cys Phe Thr Thr Asp Pro Ser Val Arg Trp Glu Tyr Cys Asn Leu
                420                 425                 430
Lys Lys Cys Ser Gly Thr Glu Ala Ser Val Val Ala Pro Pro Pro Val
            435                 440                 445
Val Leu Leu Pro Asp Val Glu Thr Pro Ser Glu Glu Asp Cys Met Phe
450                 455                 460
Gly Asn Gly Lys Gly Tyr Arg Gly Lys Arg Ala Thr Thr Val Thr Gly
465                 470                 475                 480
Thr Pro Cys Gln Asp Trp Ala Ala Gln Glu Pro His Arg His Ser Ile
                    485                 490                 495
Phe Thr Pro Glu Thr Asn Pro Arg Ala Gly Leu Glu Lys Asn Tyr Cys
                500                 505                 510
Arg Asn Pro Asp Gly Asp Val Gly Gly Pro Trp Cys Tyr Thr Thr Asn
            515                 520                 525
Pro Arg Lys Leu Tyr Asp Tyr Cys Asp Val Pro Gln Cys Ala Ala Pro
            530                 535                 540
Ser Phe Asp Cys Gly Lys Pro Gln Val Glu Pro Lys Lys Cys Pro Gly
545                 550                 555                 560
```

```
Arg Val Val Gly Gly Cys Val Ala His Pro His Ser Trp Pro Trp Gln
            565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
        610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
            645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
        690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
            725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
        770                 775                 780

Glu Gly Val Met Arg Asn Asn
785                 790

(2) INFORMATION FOR SEQ ID NO:2:

(i) SEQUENCE CHARACTERISTICS:
        (A) LENGTH: 101 amino acids
        (B) TYPE: amino acid
        (D) TOPOLOGY: linear (ii) MOLECULE TYPE:
        (A) DESCRIPTION:  protein (v) FRAGMENT TYPE:  internal (xi) SEQUENCE DESCRIPTION: SEQ ID NO:2:

Val Ala Pro Pro Val Val Leu Leu Pro Asp Val Glu Thr Pro Ser
1               5                   10                  15

Glu Glu Asp Cys Met Phe Gly Asn Gly Lys Gly Tyr Arg Gly Lys Arg
            20                  25                  30

Ala Thr Thr Val Thr Gly Thr Pro Cys Gln Asp Trp Ala Ala Gln Glu
            35                  40                  45

Pro His Arg His Ser Ile Phe Thr Pro Glu Thr Asn Pro Arg Ala Gly
        50                  55                  60

Leu Glu Lys Asn Tyr Cys Arg Asn Pro Asp Gly Asp Val Gly Gly Pro
65                  70                  75                  80

Trp Cys Tyr Thr Thr Asn Pro Arg Lys Leu Tyr Asp Tyr Cys Asp Val
                85                  90                  95

Pro Gln Cys Ala Ala
            100
```

(2) INFORMATION FOR SEQ ID NO:3:

(i) SEQUENCE CHARACTERISTICS:
        (A) LENGTH: 95 amino acids
        (B) TYPE: amino acid
        (D) TOPOLOGY: linear (ii) MOLECULE TYPE:
        (A) DESCRIPTION: protein (v) FRAGMENT TYPE: internal (xi) SEQUENCE DESCRIPTION: SEQ ID NO:3:

```
Val Leu Leu Pro Asp Val Glu Thr Pro Ser Glu Glu Asp Cys Met Phe
  1               5                  10                  15

Gly Asn Gly Lys Gly Tyr Arg Gly Lys Arg Ala Thr Thr Val Thr Gly
                 20                  25                  30

Thr Pro Cys Gln Asp Trp Ala Ala Gln Glu Pro His Arg His Ser Ile
             35                  40                  45

Phe Thr Pro Glu Thr Asn Pro Arg Ala Gly Leu Glu Lys Asn Tyr Cys
 50                  55                  60

Arg Asn Pro Asp Gly Asp Val Gly Gly Pro Trp Cys Tyr Thr Thr Asn
 65                  70                  75                  80

Pro Arg Lys Leu Tyr Asp Tyr Cys Asp Val Pro Gln Cys Ala Ala
                 85                  90                  95
```

(2) INFORMATION FOR SEQ ID NO:4:

(i) SEQUENCE CHARACTERISTICS:
        (A) LENGTH: 90 amino acids
        (B) TYPE: amino acid
        (D) TOPOLOGY: linear (ii) MOLECULE TYPE:
        (A) DESCRIPTION: protein (v) FRAGMENT TYPE: internal (xi) SEQUENCE DESCRIPTION: SEQ ID NO:4:

```
Val Glu Thr Pro Ser Glu Glu Asp Cys Met Phe Gly Asn Gly Lys Gly
  1               5                  10                  15

Tyr Arg Gly Lys Arg Ala Thr Thr Val Thr Gly Thr Pro Cys Gln Asp
                 20                  25                  30

Trp Ala Ala Gln Glu Pro His Arg His Ser Ile Phe Thr Pro Glu Thr
             35                  40                  45

Asn Pro Arg Ala Gly Leu Glu Lys Asn Tyr Cys Arg Asn Pro Asp Gly
 50                  55                  60

Asp Val Gly Gly Pro Trp Cys Tyr Thr Thr Asn Pro Arg Lys Leu Tyr
 65                  70                  75                  80

Asp Tyr Cys Asp Val Pro Gln Cys Ala Ala
                 85                  90
```

(2) INFORMATION FOR SEQ ID NO:5:

(i) SEQUENCE CHARACTERISTICS:
        (A) LENGTH: 104 amino acids
        (B) TYPE: amino acid
        (D) TOPOLOGY: linear (ii) MOLECULE TYPE:
        (A) DESCRIPTION: protein (v) FRAGMENT TYPE: internal (xi) SEQUENCE DESCRIPTION: SEQ ID NO:5:

Val Ala Pro Pro Pro Val Val Leu Leu Pro Asp Val Glu Thr Pro Ser
1               5                   10                  15

Glu Glu Asp Cys Met Phe Gly Asn Gly Lys Gly Tyr Arg Gly Lys Arg
            20                  25                  30

Ala Thr Thr Val Thr Gly Thr Pro Cys Gln Asp Trp Ala Ala Gln Glu
            35                  40                  45

Pro His Arg His Ser Ile Phe Thr Pro Glu Thr Asn Pro Arg Ala Gly
            50                  55                  60

Leu Glu Lys Asn Tyr Cys Arg Asn Pro Asp Gly Asp Val Gly Gly Pro
65                  70                  75                  80

Trp Cys Tyr Thr Thr Asn Pro Arg Lys Leu Tyr Asp Tyr Cys Asp Val
                85                  90                  95

Pro Gln Cys Ala Ala Pro Ser Phe
            100

(2) INFORMATION FOR SEQ ID NO:6:

(i) SEQUENCE CHARACTERISTICS:
        (A) LENGTH: 98 amino acids
        (B) TYPE: amino acid
        (D) TOPOLOGY: linear (ii) MOLECULE TYPE:
        (A) DESCRIPTION: protein (v) FRAGMENT TYPE: internal (xi) SEQUENCE DESCRIPTION: SEQ ID NO:6:

Val Leu Leu Pro Asp Val Glu Thr Pro Ser Glu Glu Asp Cys Met Phe
1               5                   10                  15

Gly Asn Gly Lys Gly Tyr Arg Gly Lys Arg Ala Thr Thr Val Thr Gly
            20                  25                  30

Thr Pro Cys Gln Asp Trp Ala Ala Gln Glu Pro His Arg His Ser Ile
            35                  40                  45

Phe Thr Pro Glu Thr Asn Pro Arg Ala Gly Leu Glu Lys Asn Tyr Cys
            50                  55                  60

Arg Asn Pro Asp Gly Asp Val Gly Gly Pro Trp Cys Tyr Thr Thr Asn
65                  70                  75                  80

Pro Arg Lys Leu Tyr Asp Tyr Cys Asp Val Pro Gln Cys Ala Ala Pro
                85                  90                  95

Ser Phe (2) INFORMATION FOR SEQ ID NO:7:

(i) SEQUENCE CHARACTERISTICS:
        (A) LENGTH: 93 amino acids
        (B) TYPE: amino acid
        (D) TOPOLOGY: linear (ii) MOLECULE TYPE:
        (A) DESCRIPTION: protein (v) FRAGMENT TYPE: internal (xi) SEQUENCE DESCRIPTION: SEQ ID NO:7:

Val Glu Thr Pro Ser Glu Glu Asp Cys Met Phe Gly Asn Gly Lys Gly
1               5                   10                  15

Tyr Arg Gly Lys Arg Ala Thr Thr Val Thr Gly Thr Pro Cys Gln Asp
            20                  25                  30

Trp Ala Ala Gln Glu Pro His Arg His Ser Ile Phe Thr Pro Glu Thr

```
                35                  40                  45
Asn Pro Arg Ala Gly Leu Glu Lys Asn Tyr Cys Arg Asn Pro Asp Gly
    50                  55                  60

Asp Val Gly Gly Pro Trp Cys Tyr Thr Thr Asn Pro Arg Lys Leu Tyr
65                  70                  75                  80

Asp Tyr Cys Asp Val Pro Gln Cys Ala Ala Pro Ser Phe
                85                  90

(2) INFORMATION FOR SEQ ID NO:8:

(i) SEQUENCE CHARACTERISTICS:
        (A) LENGTH: 102 amino acids
        (B) TYPE: amino acid
        (D) TOPOLOGY: linear (ii) MOLECULE TYPE:
        (A) DESCRIPTION: protein (v) FRAGMENT TYPE: internal (ix) FEATURE:
        (A) NAME/KEY: mouse sequence (xi) SEQUENCE DESCRIPTION: SEQ ID NO:8:

Val Glu Leu Pro Thr Val Ser Gln Glu Pro Ser Gly Pro Ser Asp Ser
1               5                  10                  15

Glu Thr Asp Cys Met Tyr Gly Asn Asp Lys Asp Tyr Arg Thr Lys Thr
                20                  25                  30

Ala Val Ala Ala Ala Gly Thr Pro Gly Gln Gly Trp Ala Ala Gln Glu
            35                  40                  45

Pro His Arg His Ser Ile Phe Thr Pro Gln Thr Asn Pro Arg Ala Gly
        50                  55                  60

Leu Glu Lys Asn Tyr Cys Arg Asn Pro Asp Gly Asp Val Asn Gly Pro
65                  70                  75                  80

Trp Cys Tyr Thr Thr Asn Pro Arg Ser Leu Tyr Asp Tyr Cys Asp Ile
                85                  90                  95

Pro Leu Cys Ala Ser Ala
            100

(2) INFORMATION FOR SEQ ID NO:9:

(i) SEQUENCE CHARACTERISTICS:
        (A) LENGTH: 100 amino acids
        (B) TYPE: amino acid
        (D) TOPOLOGY: linear (ii) MOLECULE TYPE:
        (A) DESCRIPTION: protein (v) FRAGMENT TYPE: internal (ix) FEATURE:
        (A) NAME/KEY: monkey sequence (xi) SEQUENCE DESCRIPTION: SEQ ID NO:9:

Ala Ala Pro Pro Pro Val Ala Gln Leu Pro Asp Ala Glu Thr Pro Ser
1               5                  10                  15

Glu Glu Asp Cys Met Phe Gly Asn Gly Lys Gly Tyr Arg Gly Lys Lys
                20                  25                  30

Ala Thr Thr Val Thr Gly Thr Pro Cys Gln Asp Trp Ala Ala Gln Glu
            35                  40                  45

Pro His Ser His Arg Ile Phe Thr Pro Glu Thr Asn Pro Arg Ala Gly
        50                  55                  60
```

```
Leu Glu Lys Asn Tyr Cys Arg Asn Pro Asp Gly Asp Val Gly Pro
65                  70                  75                  80

Trp Cys Tyr Thr Thr Asn Pro Arg Ser Leu Phe Asp Tyr Cys Asp Val
                    85                  90                  95

Pro Gln Cys Ala
            100
```

(2) INFORMATION FOR SEQ ID NO:10:

(i) SEQUENCE CHARACTERISTICS:
        (A) LENGTH: 97 amino acids
        (B) TYPE: amino acid
        (D) TOPOLOGY: linear (ii) MOLECULE TYPE:
        (A) DESCRIPTION: protein (v) FRAGMENT TYPE: internal (ix) FEATURE:
        (A) NAME/KEY: bovine sequence (xi) SEQUENCE DESCRIPTION: SEQ ID NO:10:

```
Pro Ala Ala Pro Gln Ala Pro Gly Val Glu Asn Pro Pro Glu Ala Asp
1               5                   10                  15

Cys Met Ile Gly Thr Gly Lys Ser Tyr Arg Gly Lys Lys Ala Thr Thr
                20                  25                  30

Val Ala Gly Val Pro Cys Gln Glu Trp Ala Ala Gln Glu Pro His His
                35                  40                  45

His Ser Ile Phe Thr Pro Glu Thr Asn Pro Gln Ser Gly Leu Glu Arg
        50                  55                  60

Asn Tyr Cys Arg Asn Pro Asp Gly Asp Val Asn Gly Pro Trp Cys Tyr
65                  70                  75                  80

Thr Met Asn Pro Arg Ser Leu Phe Asp Tyr Cys Asp Val Pro Gln Cys
                85                  90                  95

Glu
```

(2) INFORMATION FOR SEQ ID NO:11:

(i) SEQUENCE CHARACTERISTICS:
        (A) LENGTH: 101 amino acids
        (B) TYPE: amino acid
        (D) TOPOLOGY: linear (ii) MOLECULE TYPE:
        (A) DESCRIPTION: protein (v) FRAGMENT TYPE: internal (ix) FEATURE:
        (A) NAME/KEY: porcine sequence (xi) SEQUENCE DESCRIPTION: SEQ ID NO:11:

```
Thr Asn Phe Pro Ala Ile Ala Gln Val Pro Ser Val Glu Asp Leu Ser
1               5                   10                  15

Glu Glu Asp Cys Met Phe Gly Asn Gly Lys Arg Tyr Arg Gly Lys Arg
                20                  25                  30

Ala Thr Thr Val Ala Gly Val Pro Cys Gln Glu Trp Ala Ala Gln Glu
                35                  40                  45

Pro His Arg His Ser Ile Phe Thr Pro Glu Thr Asn Pro Arg Ala Gly
        50                  55                  60

Leu Glu Lys Asn Tyr Cys Arg Asn Pro Asp Gly Asp Asp Asn Gly Pro
65                  70                  75                  80
```

```
Trp Cys Tyr Thr Thr Asn Pro Gln Lys Leu Phe Asp Tyr Cys Asp Val
            85                  90                  95

Pro Gln Cys Val Thr
            100
```

(2) INFORMATION FOR SEQ ID NO:12:

(i) SEQUENCE CHARACTERISTICS:
        (A) LENGTH: 2497 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

```
CATCCTGGGA TTGGGACCCA CTTTCTGGGC ACTGCTGGCC AGTCCCAAAA TGGAACATAA     60
GGAAGTGGTT CTTCTACTTC TTTTATTTCT GAAATCAGGT CAAGGAGAGC CTCTGGATGA    120
CTATGTGAAT ACCCAGGGGG CTTCACTGTT CAGTGTCACT AAGAAGCAGC TGGGAGCAGG    180
AAGTATAGAA GAATGTGCAG CAAAATGTGA GGAGGACGAA GAATTCACCT GCAGGGCATT    240
CCAATATCAC AGTAAAGAGC AACAATGTGT GATAATGGCT GAAAACAGGA AGTCCTCCAT    300
AATCATTAGG ATGAGAGATG TAGTTTTATT TGAAAAGAAA GTGTATCTCT CAGAGTGCAA    360
GACTGGGAAT GGAAAGAACT ACAGAGGGAC GATGTCCAAA ACAAAAAATG GCATCACCTG    420
TCAAAAATGG AGTTCCACTT CTCCCCACAG ACCTAGATTC TCACCTGCTA CACACCCCTC    480
AGAGGGACTG GAGGAGAACT ACTGCAGGAA TCCAGACAAC GATCCGCAGG GGCCCTGGTG    540
CTATACTACT GATCCAGAAA AGAGATATGA CTACTGCGAC ATTCTTGAGT GTGAAGAGGA    600
ATGTATGCAT TGCAGTGGAG AAAACTATGA CGGCAAAATT TCCAAGACCA TGTCTGGACT    660
GGAATGCCAG GCCTGGGACT CTCAGAGCCC ACACGCTCAT GGATACATTC CTTCCAAATT    720
TCCAAACAAG AACCTGAAGA AGAATTACTG TCGTAACCCC GATAGGGAGC TGCGGCCTTG    780
GTGTTTCACC ACCGACCCCA ACAAGCGCTG GGAACTTTGT GACATCCCCC GCTGCACAAC    840
ACCTCCACCA TCTTCTGGTC CCACCTACCA GTGTCTGAAG GGAACAGGTG AAAACTATCG    900
CGGGAATGTG GCTGTTACCG TGTCCGGGCA CACCTGTCAG CACTGGAGTG CACAGACCCC    960
TCACACACAT AACAGGACAC CAGAAAACTT CCCCTGCAAA AATTTGGATG AAAACTACTG   1020
CCGCAATCCT GACGGAAAAA GGGCCCCATG GTGCCATACA ACCAACAGCC AAGTGCGGTG   1080
GGAGTACTGT AAGATACCGT CCTGTGACTC CTCCCCAGTA TCCACGGAAC AATTGGCTCC   1140
CACAGCACCA CCTGAGCTAA CCCCTGTGGT CCAGGACTGC TACCATGGTG ATGGACAGAG   1200
CTACCGAGGC ACATCCTCCA CCACCACCAC AGGAAAGAAG TGTCAGTCTT GGTCATCTAT   1260
GACACCACAC CGGCACCAGA AGACCCCAGA AAACTACCCA AATGCTGGCC TGACAATGAA   1320
CTACTGCAGG AATCCAGATG CCGATAAAGG CCCCTGGTGT TTTACCACAG ACCCCAGCGT   1380
CAGGTGGGAG TACTGCAACC TGAAAAAATG CTCAGGAACA GAAGCGAGTG TTGTAGCACC   1440
TCCGCCTGTT GTCCTGCTTC CAGATGTAGA GACTCCTTCC GAAGAAGACT GTATGTTTGG   1500
GAATGGGAAA GGATACCGAG GCAAGAGGGC GACCACTGTT ACTGGGACGC CATGCCAGGA   1560
CTGGGCTGCC CAGGAGCCCC ATAGACACAG CATTTTCACT CCAGAGACAA ATCCACGGGC   1620
GGGTCTGGAA AAAAATTACT GCCGTAACCC TGATGGTGAT GTAGGTGGTC CCTGGTGCTA   1680
CACGACAAAT CCAAGAAAAC TTTACGACTA CTGTGATGTC CCTCAGTGTG CGGCCCCTTC   1740
ATTTGATTGT GGGAAGCCTC AAGTGGAGCC GAAGAAATGT CCTGGAAGGG TTGTAGGGGG   1800
GTGTGTGGCC CACCCACATT CCTGGCCCTG GCAAGTCAGT CTTAGAACAA GGTTTGGAAT   1860
```

```
GCACTTCTGT GGAGGCACCT TGATATCCCC AGAGTGGGTG TTGACTGCTG CCCACTGCTT    1920

GGAGAAGTCC CCAAGGCCTT CATCCTACAA GGTCATCCTG GGTGCACACC AAGAAGTGAA    1980

TCTCGAACCG CATGTTCAGG AAATAGAAGT GTCTAGGCTC TTCTTGGAGC CCACACGAAA    2040

AGATATTGCC TTGCTAAAGC TAAGCAGTCC TGCCGTCATC ACTGACAAAG TAATCCCAGC    2100

TTGTCTGCCA TCCCCAAATT ATGTGGTCGC TGACCGGACC GAATGTTTCG TCACTGGCTG    2160

GGGAGAAACC CAAGGTACTT TTGGAGCTGG CCTTCTCAAG GAAGCCCAGC TCCCTGTGAT    2220

TGAGAATAAA GTGTGCAATC GCTATGAGTT TCTGAATGGA AGAGTCCAAT CCACCGAACT    2280

CTGTGCTGGG CATTTGGCCG GAGGCACTGA CAGTTGCCAG GGTGACAGTG GAGGTCCTCT    2340

GGTTTGCTTC GAGAAGGACA AATACATTTT ACAAGGAGTC ACTTCTTGGG GTCTTGGCTG    2400

TGCACGCCCC AATAAGCCTG GTGTCTATGT TCGTGTTTCA AGGTTTGTTA CTTGGATTGA    2460

GGGAGTGATG AGAAATAATT AATTGGACGG GAGACAG                             2497

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear (ii) MOLECULE TYPE:
        (A) DESCRIPTION: peptide (v) FRAGMENT TYPE: internal fragment (ix) FEATURE:
        (A) OTHER INFORMATION: Tyr number 7 is 3-I-Tyr.

(xi) SEQUENCE DESCRIPTION: SEQ ID NO:13:

Pro Arg Lys Leu Tyr Asp Tyr
1               5

(2) INFORMATION FOR SEQ ID NO:14:

(i) SEQUENCE CHARACTERISTICS:
        (A) LENGTH: 7 amino acids
        (B) TYPE: amino acid
        (D) TOPOLOGY: linear (ii) MOLECULE TYPE:
        (A) DESCRIPTION: peptide (v) FRAGMENT TYPE: internal fragment (ix) FEATURE:
        (A) OTHER INFORMATION: Tyr number 5 is 3-I-Tyr.

(xi) SEQUENCE DESCRIPTION: SEQ ID NO:14:

Pro Arg Lys Leu Tyr Asp Tyr
1               5
```